(12) United States Patent
Edlund et al.

(10) Patent No.: US 12,373,948 B2
(45) Date of Patent: Jul. 29, 2025

(54) METHOD TO DETECT AND MEASURE A WOUND SITE ON A MOBILE DEVICE

(71) Applicant: KCI Manufacturing Unlimited Company, Westmeath (IE)

(72) Inventors: Chester Edlund, San Antonio, TX (US); Brian Lawrence, San Antonio, TX (US); Christopher J. Sandroussi, San Antonio, TX (US); James Laird, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 92 days.

(21) Appl. No.: 18/289,856

(22) PCT Filed: May 13, 2022

(86) PCT No.: PCT/IB2022/054468
§ 371 (c)(1),
(2) Date: Nov. 7, 2023

(87) PCT Pub. No.: WO2022/248964
PCT Pub. Date: Dec. 1, 2022

(65) Prior Publication Data
US 2024/0249406 A1 Jul. 25, 2024

Related U.S. Application Data

(60) Provisional application No. 63/194,541, filed on May 28, 2021.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0077* (2013.01); *A61B 5/7455* (2013.01);
(Continued)

(58) Field of Classification Search
None
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Samira Monshi

(57) ABSTRACT

A system for measuring a wound site including an image capture device, a touchscreen, a vibration motor, and a processor. The image capture device may be configured to capture a digital image and capture a depth map associated with the digital image. The processor may be configured to determine abounding box of the wound site, determine a wound mask, determine a wound boundary, determine whether the wound boundary is aligned within a camera frame, and generate a wound map. The processor and vibration motor may be configured to provide a series of (Continued)

vibrations in response to the processor determining that the wound is aligned within the camera frame.

20 Claims, 16 Drawing Sheets

(51) Int. Cl.
| | |
|---|---|
| *G06T 3/40* | (2006.01) |
| *G06T 7/11* | (2017.01) |
| *G06T 7/13* | (2017.01) |
| *G06T 7/136* | (2017.01) |
| *G06T 7/50* | (2017.01) |
| *G06T 7/62* | (2017.01) |
| *G06V 10/771* | (2022.01) |
| *G06V 10/82* | (2022.01) |
| *H04N 23/60* | (2023.01) |
| *H04N 23/63* | (2023.01) |

(52) U.S. Cl.
CPC .............. *A61B 5/7475* (2013.01); *G06T 3/40* (2013.01); *G06T 7/11* (2017.01); *G06T 7/13* (2017.01); *G06T 7/136* (2017.01); *G06T 7/50* (2017.01); *G06T 7/62* (2017.01); *G06V 10/771* (2022.01); *G06V 10/82* (2022.01); *H04N 23/631* (2023.01); *H04N 23/635* (2023.01); *H04N 23/64* (2023.01); *G06T 2207/10028* (2013.01); *G06T 2207/10048* (2013.01); *G06T 2207/20084* (2013.01); *G06T 2207/30088* (2013.01); *G06V 2201/03* (2022.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |

(56) References Cited

U.S. PATENT DOCUMENTS

| | | | |
|---|---|---|---|
| 2002/0143286 | A1 | 10/2002 | Tumey |
| 2013/0215975 | A1* | 8/2013 | Samuelsson ........... H04N 19/58 |
| | | | 375/240.25 |
| 2014/0163491 | A1 | 6/2014 | Schuessler et al. |
| 2015/0080788 | A1 | 3/2015 | Blott et al. |
| 2015/0150457 | A1 | 6/2015 | Wu et al. |
| 2019/0008387 | A1* | 1/2019 | Godavarty ........... A61B 5/7435 |
| 2019/0388057 | A1 | 12/2019 | Shen et al. |
| 2023/0022554 | A1* | 1/2023 | Peterson .............. A61B 5/6898 |

FOREIGN PATENT DOCUMENTS

| | | |
|---|---|---|
| AU | 755496 B2 | 12/2002 |
| CA | 2005436 A1 | 6/1990 |
| DE | 2640413 A1 | 3/1978 |
| DE | 4306478 A1 | 9/1994 |
| DE | 29504378 U1 | 9/1995 |
| EP | 0100148 A1 | 2/1984 |
| EP | 117632 A2 | 9/1984 |
| EP | 161865 A2 | 11/1985 |
| EP | 358302 A2 | 3/1990 |
| EP | 1018967 A1 | 7/2000 |
| GB | 692578 A | 6/1953 |
| GB | 2195255 A | 4/1988 |
| GB | 2197789 A | 6/1988 |
| GB | 2220357 A | 1/1990 |
| GB | 2235877 A | 3/1991 |
| GB | 2329127 A | 3/1999 |
| GB | 2333965 A | 8/1999 |
| JP | 4129536 B2 | 8/2008 |
| SG | 71559 | 4/2002 |
| WO | 80/02182 A1 | 10/1980 |
| WO | 8704626 A1 | 8/1987 |
| WO | 90010424 A1 | 9/1990 |
| WO | 93009727 A1 | 5/1993 |
| WO | 94020041 A1 | 9/1994 |
| WO | 9605873 A1 | 2/1996 |
| WO | 9718007 A1 | 5/1997 |
| WO | 9913793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al. "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Juszczyk Jan Maria et al: "Wound 3D Geometrical Feature Estimation Using Poisson Reconstruction" IEEE Access, IEEE, USA, vol. 9, Oct. 30, 2020 (Oct. 30, 2020), pp. 7894-7907.
Wang Chuanbo et al: "Fully automatic wound segmentation with deep convolutional neural networks", Scientific Reports, vol. 10, No. 1, Dec. 1, 2020 (Dec. 1, 2020).
PCT International Search Report/ Written Opinion for International Application No. PCT/IB2022/054468, mailed Sep. 22, 2022.

\* cited by examiner

METHOD TO DETECT AND MEASURE A WOUND SITE ON A MOBILE DEVICE

CROSS-REFERENCE TO RELATED APPLICATIONS

This application claims the benefit of priority to U.S. Provisional Application No. 63/194,541, filed on May 28, 2021, which is incorporated herein by reference in its entirety.

TECHNICAL FIELD

The invention set forth in the appended claims relates generally to tissue treatment systems. More particularly, but without limitation, the present disclosure relates to systems and methods for accomplishing acquisition and processing of wound images, as well as photogrammetry.

BACKGROUND

A wound is generally defined as a break in the epithelial integrity of the skin. Such an injury, however, may be much deeper, including the dermis, subcutaneous tissue, fascia, muscle, and even bone. Proper wound healing is a highly complex, dynamic, and coordinated series of steps leading to tissue repair. Acute wound healing is a dynamic process involving both resident and migratory cell populations acting in a coordinated manner within the extra-cellular matrix environment to repair the injured tissues. Some wounds fail to heal in this manner (for a variety of reasons) and may be referred to as chronic wounds.

Following tissue injury, the coordinated healing of a wound will typically involve four overlapping but well-defined phases: hemostasis, inflammation, proliferation, and remodeling. Hemostasis involves the first steps in wound response and repair which are bleeding, coagulation, and platelet and complement activation. Inflammation peaks near the end of the first day. Cell proliferation occurs over the next 7-30 days and involves the time period over which wound area measurements may be of most benefit. During this time, fibroplasia, angiogenesis, re-epithelialization, and extra-cellular matrix synthesis occur. The initial collagen formation in a wound typically peaks in approximately 7 days. The wound re-epithelialization occurs in about 48 hours under optimal conditions, at which time the wound may be completely sealed. A healing wound may have 15% to 20% of full tensile strength at 3 weeks and 60% of full strength at 4 months. After the first month, a degradation and remodeling stage begins, wherein cellularity and vascularity decrease and tensile strength increases. Formation of a mature scar often requires 6 to 12 months.

There are various wound parameters that may assist a clinician in determining and tracking healing progress of a wound. For example, wound dimensions, including wound area and volume measurements, may provide a clinician with knowledge as to whether or not a wound is healing and, if the wound is healing, how rapidly the wound is healing. Wound assessment is an important process to properly treating a wound, as improper or incomplete assessment may result in a wide variety of complications.

While wound measurements may provide valuable parameters for helping a clinician assess wound healing progress, the size of the wound may not provide a clinician with a full picture to fully assess whether or how a wound is healing. For example, while the size of a wound may be reduced during treatment, certain parts of a wound may become infected, or wound healing may become stalled, due to infection or comorbidity. A clinician may often-times examine the wound bed for indication of wound healing, such as formation of granulation tissue, early stage epithelial growth, or look for signs and symptoms of infection. Wound tissue includes a wound bed and peri-wound areas and wound edges. Health of a wound may be determined by color of tissue, with certain problems often presenting with distinct colors at the wound. For example, normal granulation tissue typically has a red, shiny textured appearance and bleeds readily, whereas necrotic tissue (i.e., dead tissue) may either be yellow-gray and soft, generally known as "slough" tissue, or hard and blackish-brown in color, generally known as "eschar" tissue. A clinician may observe and monitor these and other wound tissues to determine wound healing progress of the overall wound, as well as specific wound regions.

Because wound treatment can be costly in both materials and professional care time, a treatment that is based on an accurate assessment of the wound and the wound healing process can be essential.

BRIEF SUMMARY

New and useful systems, apparatuses, and methods for wound image analysis are set forth in the appended claims. Illustrative embodiments are also provided to enable a person skilled in the art to make and use the claimed subject matter.

For example, a system for measuring a wound site is presented. The system may include an image capture device, a touchscreen, a vibration motor, and a processor. The image capture device may be configured to capture a digital image and capture a depth map associated with the digital image. The processor may be configured to determine a bounding box of the wound site by processing the digital image with a first trained neural network, determine a wound mask by processing the digital image with a second trained neural network, determine a wound boundary from the wound mask, determine whether the wound boundary is aligned within a camera frame, and generate a wound map from the depth map, wound mask, and wound boundary. The processor and vibration motor may be configured to provide a series of vibrations at the vibration motor in response to the processor determining that the wound is aligned within the camera frame.

According to exemplary embodiments, the processor may be further configured to scale the digital image to generate a scaled image, pad the scaled image to generate a padded image, determine a plurality of possible wound regions by inputting the padded image into the first trained neural network, and determine the bounding box by applying a non-maximum suppression algorithm to the plurality of possible wound regions. In some examples, the processor may be further configured to select a selected possible wound regions from the plurality of possible wound regions. The selected possible wound region may have a highest objectiveness score within the plurality of possible wound regions. The processor may be further configured to move the selected possible wound region to a set of probable wound regions, calculate an Intersection over Union of the selected possible wound region with each possible wound region in the plurality of possible wound regions, and remove each possible wound region in the plurality of possible wound regions having an Intersection over Union with the selected possible wound region lower than a threshold.

In some examples, the processor may be further configured to scale the digital image to generate a scaled image, normalize pixel values of the scaled image to generate a normalized image, determine a raw mask by inputting the normalized image into the second trained neural network, and transform the raw mask into a wound mask. In some embodiments, the processor may be further configured to select a pixel value threshold, set values of raw mask pixels greater than the pixel value threshold to 1, and set values of raw mask pixels not greater than the pixel value threshold to 0. In exemplary embodiments, the processor may be further configured to set values of raw mask pixels having a value of 1 to 255 and output the raw mask as the wound mask.

In other features, the processor may be further configured to generate a wound surface mask by interpolating depth information of portions of the depth map outside of the wound boundary, generate wound depth data by calculating a depth difference between the wound surface map and the wound map, calculate a mathematical length of the wound and a mathematical width of the wound from the wound map, and calculate a wound mathematical volume from the mathematical length of the wound, the mathematical width of the wound, and depth data of the wound map.

Alternatively, in other example embodiments, the processor may be further configured to assign an orientation axis to the wound map, calculate a standard length of the wound and a standard width of the wound from the wound map and the orientation axis, determine a standard depth of the wound from the wound map, and calculate a standard wound volume from the standard length of the wound, the standard width of the wound, and the standard depth of the wound.

In some examples, the series of vibrations may include two quick vibrations with ascending intensity. In other features, the processor and touchscreen may be configured to display a visual indicator on the touchscreen in response to the processor determining that the wound is aligned within the camera frame. According to some examples, the system may further include a speaker assembly. The processor and the speaker assembly may be configured to output an audible alert from the speaker assembly in response to the processor determining that the wound is aligned within the camera frame. In some examples, the processor and speaker assembly may be configured to output an audible alert from the speaker assembly in response to the processor determining that the wound is not aligned within the camera frame.

In other features, the image capture device may include an electro-optical camera, an infrared camera, and a light emitting module. In some examples, the light emitting module may be configured to emit multiple light rays according to a pattern. In some examples, the image capture device may include an electro-optical camera and a time-of-flight camera.

A non-transitory computer-readable medium including executable instructions for performing steps in a method for measuring a wound site is also described. The executable instructions may configure a processor to receive a digital image, receive a depth map associated with the digital image, determine a bounding box of the wound site by processing the digital image with a first trained neural network, determine a wound mask by processing the digital image with a second trained neural network, determine a wound boundary from the wound mask, determine whether the wound boundary is aligned within a camera frame, and generate a wound map from the depth data, wound mask, and wound boundary. In some examples, the executable instructions may further configure the controller to output a signal to generate a first series of vibrations at a vibration motor in response to the processor determining that the wound is aligned within the camera frame.

A method for measuring a wound side is also described. The method may include capturing a digital image of the wound site with an image capture device, capturing a depth map associated with the digital image with the image capture device, determining a bounding box of the wound site by processing the digital image with a first trained neural network, determining a wound mask of the wound site by processing the digital image with a second neural network, determining a wound boundary from the wound mask, generating a wound map from the depth map, wound mask, and wound boundary, determining whether the wound boundary is aligned within a camera frame, and providing a series of vibrations at a vibration motor if the wound is aligned within the camera frame. In some examples, the series of vibrations may include two quick vibrations with ascending intensity. In some examples, the method may further include outputting an audible alert from a speaker assembly if the wound boundary is aligned within the camera frame.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
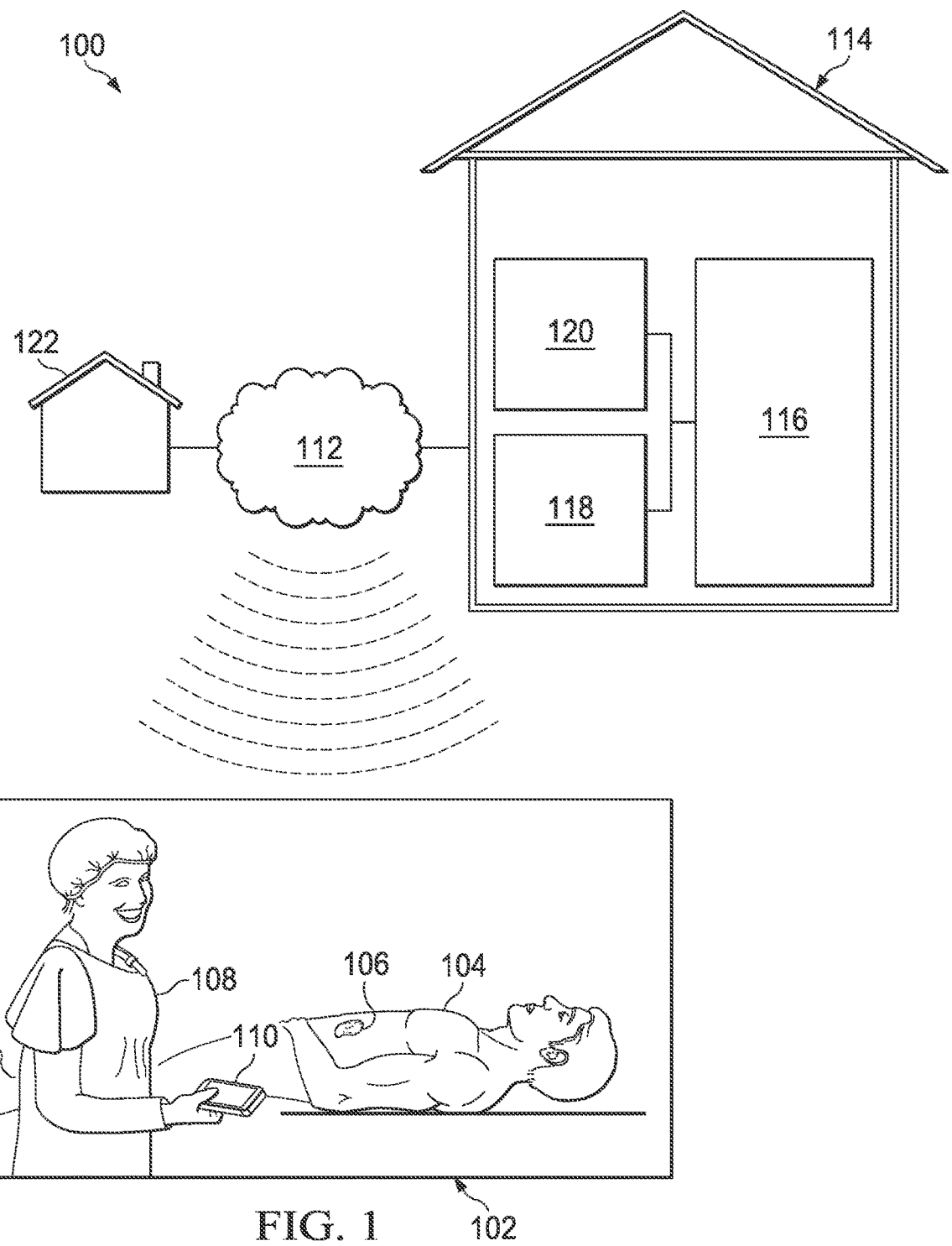
FIG. 1 is an illustration of a therapy network in accordance with an exemplary embodiment.

FIG. 1 is a schematic diagram of an example embodiment of a therapy network 100 that can support a wound imaging and diagnostic application in accordance with this specification. The therapy network 100 may include a clinical setting 102, which may include an environment where a patient 104 with a tissue site 106 may be evaluated and/or treated by a clinician 108. The clinician 108 may use a mobile device 110, in conjunction with the wound imaging and diagnostic application, to capture, edit, and analyze images related to the tissue site 106.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The term "clinician" is used herein as meaning any medical professional, user, family member of a patient, or patient who interacts or interfaces with the various aspects of care related to a tissue site.

A mobile device for the purposes of this application may include any combination of a computer or microprocessor. The computer or microprocessor may be programmed to implement one or more software algorithms for achieving the functionality described in the specification and corresponding figures. The mobile device, such as mobile device 110, may also include a communication device, and may be a smartphone, a tablet computer, or other device that is capable of storing a software application programmed for a specific operating system (e.g., iOS, Android, and Windows). The mobile device 110 may also include an electronic display and a graphical user interface (GUI), for providing visual images and messages to a user, such as a clinician or patient. The mobile device 110 may be configured to communicate with one or more networks 112 of the therapy network 100. In some embodiments, the mobile device 110 may include a cellular modem and may be configured to communicate with the network(s) 112 through a cellular connection. In other embodiments, the mobile device 110 may include a Bluetooth® radio or other wireless radio technology for communicating with the network(s) 112. The mobile device 110 may be configured to transmit data related to the tissue site 106 of the patient 104.

The therapy network 100 may also include a support center 114 that may be in communication with the mobile device 110 through network(s) 112. For example, the mobile device 110 may be configured to transmit data through network(s) 112 to the support center 114. The support center 114 may support a wound imaging database 116. In some embodiments, the support center 114 may include both a clinical support center 118 and a technical support center 120. The clinical support center 118 may function as a centralized center for clinicians to contact regarding questions they may have related to imaging of specific wounds with which they may be presented. The technical support center 120 may serve as a contact point for solving technical issues with use of the wound imaging and diagnostic application.

The therapy network 100 may also include other entities that may communicate with clinical settings, mobile devices, and support centers through network(s) 112. For example, the therapy network 100 may include a third party 122. In some embodiments, the third party 122 may be an image-processing vendor. Various image-processing vendors may be included as part of the therapy network 100, to provide expertise and support for wound images that may be particularly unique or challenging to process and analyze. Such image-processing vendors may offer one or more additional software packages that may be used for processing specific aspects of captured wound images. In these embodiments, a representative in the clinical support center 118 may determine that a particular image requires the additional processing expertise offered by a specific image-processing vendor and may route the image file(s) to that vendor. In some embodiments, the wound imaging and diagnostic application may prompt the user, such as the clinician, for routing the image to the third-party vendor, or in some cases, may be configured to automatically route the image to one or more particular image-processing vendors.

Figure 2:
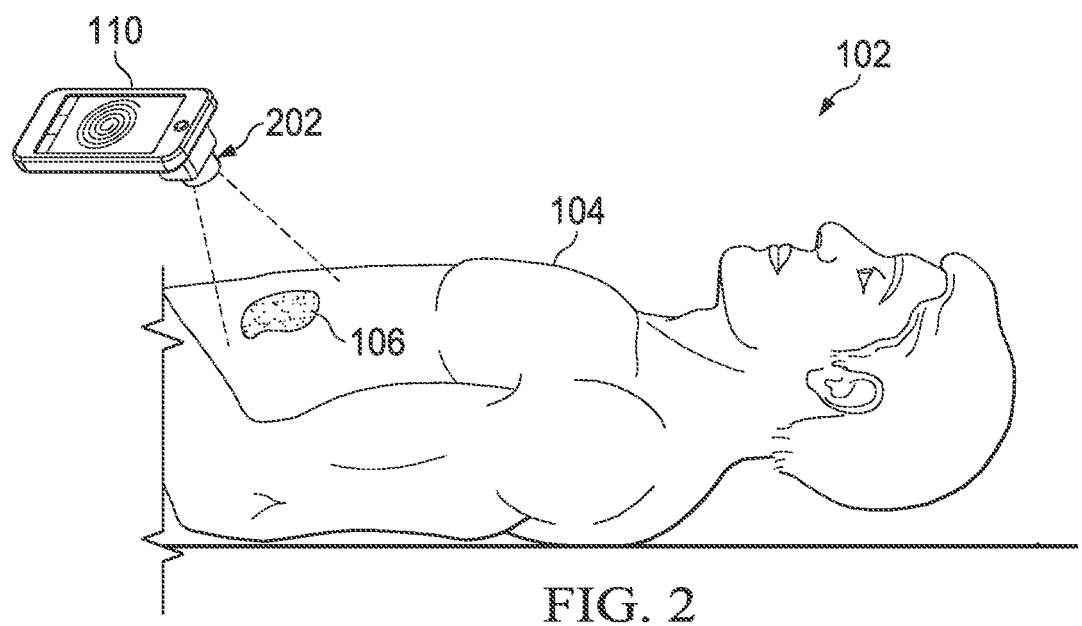
FIG. 2 is a perspective view illustrating additional details that may be associated with some example embodiments of the therapy network of FIG. 1.

Referring to FIG. 2, an exemplary patient environment, such as clinical setting 102, is shown with the patient 104 having a tissue site 106. Mobile device 110 is also shown, with an image capture device 202, which may be utilized to capture an image of the tissue site 106. In some examples, the captured image may include one or more two-dimensional digital images, such as a raster graphic including a dot matrix data structure representing a grid of pixels which may be viewed via a bitmapped display. In some examples, the captured image may include a stream of consecutive still images, such as a video. In some examples, the captured image may also include distance or depth information associated with each pixel of the captured image. The captured image may then be transmitted from the image capture device 202 to the mobile device 110. The image capture device 202 may be a digital camera, including a digital camera with a radiation source, such as an infrared or laser emitter configured to emit a pattern onto the tissue site 106. In some examples, the image capture device 202 may be a digital camera, including a digital camera with a time-of-flight camera. In general, to expedite capturing and working with an image of the tissue site 106, the image capture device 202 may be in the form of a digital camera that is configured to be physically connected to the mobile device 110 and may communicate with the mobile device 110 using a wired connection. In some examples, the image capture device 202 may be configured to be wirelessly connected to the mobile device 110. In some examples, the image capture device 202 may utilize memory device (not shown) that may be transferred between electronic devices. The memory device may include an electronic non-volatile computer memory storage medium capable of being electronically erased and reprogrammed, such as flash memory. The memory device may include any other memory device with which the mobile device 110 may be compatible.

As previously discussed, the image capture device 202 may be used to capture images which may be incorporated into the wound imaging and diagnostic application. The captured images may then be shared among interested parties, such as the clinician, image processing vendors, and the patient. Wound images captured by the image capture device 302 may be used by the wound imaging and diagnostic application to determine a depth map associated with each captured wound image, determine a bounding box of the wound, determine a wound mask, calculate a wound boundary, generate a wound map, and calculate various characteristics of the wound. As also previously mentioned, the image capture device 202 may include a three-dimensional camera connected to the mobile device 110, which may also be used to capture wound images that may be used by the wound imaging and diagnostic application to automatically determine one or more wound dimensions and upload the dimensions to the proper data fields in the wound imaging application. Additionally, the image capture device 202 may be used to capture images of the tissue site 106 over time, in order for a clinician, a patient, or other interested party to monitor the healing progress of the tissue site 106. Users, such as clinicians, may also have the ability to upload images previously taken, which may be stored in a secure gallery on the mobile device 110. Tissue site images captured by the image capture device 302 may each be stored in an image database, such as wound imaging database 116, associated with the wound imaging and diagnostic application and therapy network 100.

Figure 3:
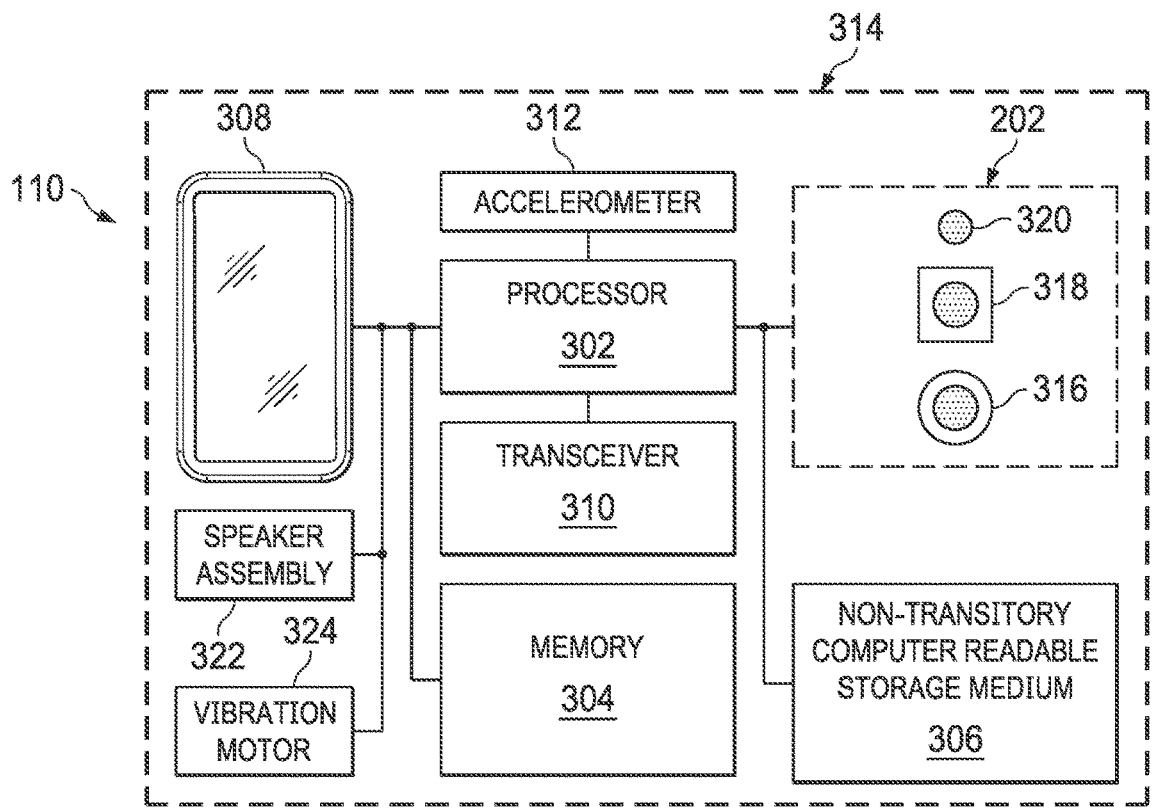
FIG. 3 is a schematic diagram illustrating some examples of the mobile device of FIGS. 1 and 2 and the image capture device of FIG. 2.

FIG. 3 is a schematic diagram illustrating some examples of the mobile device 110 of FIGS. 1 and 2 and the image capture device 202 of FIG. 2. As previously described, the mobile device 110 may comprise computer or a microprocessor. For example, the mobile device 110 may include a processor 302, a memory 304, such as random-access memory (RAM), and a non-transitory computer readable storage medium 306, such as a hard disk drive (HDD), single-level cell (SLC) NAND flash, multi-level cell (MLC) NAND flash, triple-level cell (TLC) NAND flash, quad-level cell (QLC) NAND flash, NOR flash, or any other suitable storage medium. The mobile device 110 may also include an electronic display, such as touchscreen 308. As previously described, the mobile device 110 may also be configured to communicate with one or more networks 112 of the therapy network 100, and may include a communication device, such as a cellular modem or transceiver 310. In some examples, the mobile device 110 may also include an accelerometer 312, such as a three-axis accelerometer. According to some examples, the processor 302, memory 304, non-transitory computer readable storage medium 306, transceiver 310, and accelerometer 312 may be contained within a housing 314. In some examples, the image capture device 202 and the touchscreen 308 may be coupled to the housing 314. According to illustrative embodiments, the image capture device 202, memory 304, non-transitory computer readable storage medium 306, touchscreen 308, transceiver 310, and accelerometer 312 may each be operatively coupled to the processor 302 and/or each other.

As illustrated in the example of FIG. 3, the image capture device 202 may include a first camera module 316, a second camera module 318, and a light emitting module 320. In some examples, the first camera module 316 may be an electro-optical camera suitable for detecting and converting visible light into an electronic signal, and the second camera module 318 may be an infrared camera suitable for detecting and converting infrared light into an electronic signal. The light emitting module 320 may be configured to emit multiple light rays, such as multiple rays of infrared light, towards an object to be detected. In operation, the light emitting module 320 may emit the multiple light rays according to a pattern, such that a spacing between each ray of the multiple light rays at a given distance is known. Thus, when the multiple light rays are emitted onto the object to be detected, the distance from the light emitting module 320 and various points on the object to be detected may be calculated by measuring the spacing between the points of light from the multiple light rays projected onto the surface of the object to be detected, and a three-dimensional depth map of the surface of the object to be detected may be generated.

As shown in FIG. 3, in some examples, the mobile device 110 may also contain an audio output system, such as a speaker assembly 322. The speaker assembly 322 may contain a digital-to-analog converter (DAC) operatively coupled to the processor 302, an amplifier operatively coupled to the DAC, and/or one or more speakers operatively coupled to the amplifier or directly to the DAC. According to the illustrative embodiments, the mobile device 110 may also contain a haptic feedback system, such as a vibration motor 324. The vibration motor 318 may be operatively coupled to the processor 324.

Figure 4:
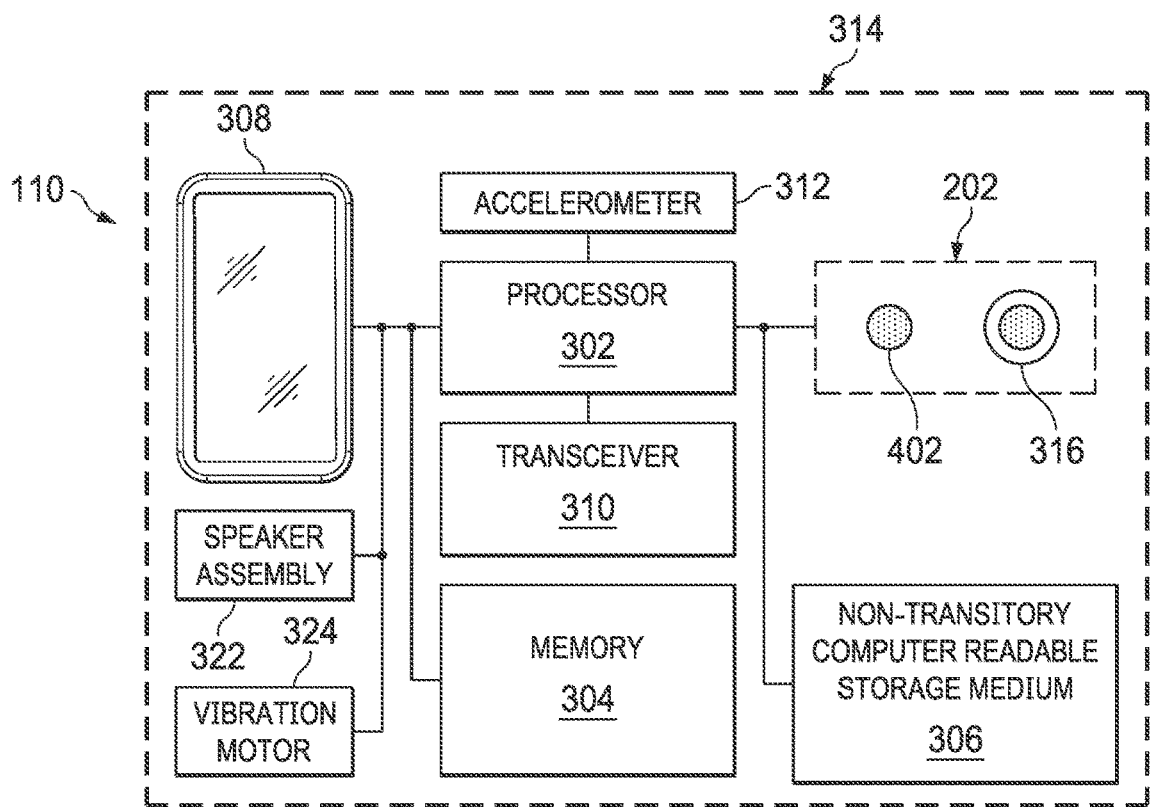
FIG. 4 is a schematic diagram illustrating additional examples of the mobile device of FIGS. 1 and 2 and the image capture device 202 of FIG. 2.

FIG. 4 is a schematic diagram illustrating additional examples of the mobile device 110 of FIGS. 1 and 2 and the image capture device 202 of FIG. 2. As illustrated in FIG. 4, some examples of the image capture device 202 may include a time-of-flight camera 402. For example, the time-of-flight camera 402 may be any camera suitable for producing a depth map of the surface of the object to be detected through light detection.

Figure 5A:
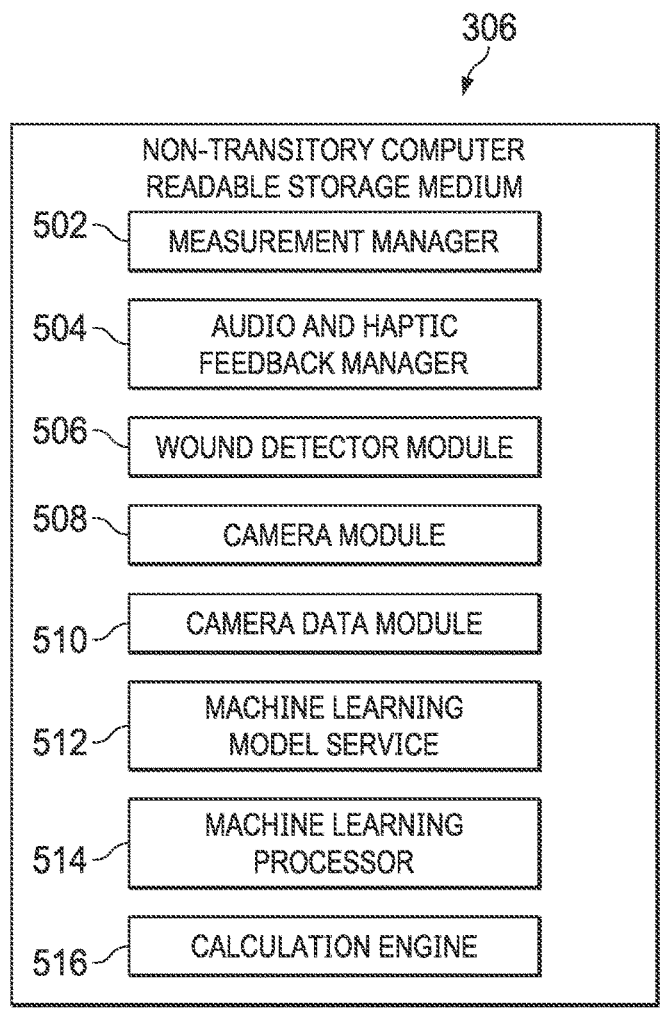
FIG. 5A is a schematic diagram illustrating examples of modules which may be stored on the non-transitory computer readable storage medium of FIG. 3 and which may be accessed by the processor and other components of the mobile device of FIGS. 1, 2, and 3.

FIG. 5A is a schematic diagram illustrating examples of modules which may be stored on the non-transitory computer readable storage medium 306 of FIG. 3 and which may be accessed by the processor 302 and other components of the mobile device 110 of FIGS. 1, 2, and 3. For example, the non-transitory computer readable storage medium 306 may contain a measurement management module, such as measurement manager 502, a module managing audio and haptic feedback provided to the user, such as an audio and haptic feedback manager 504, a module responsible for the detection of wounds on images from the image capture device 202, such as a wound detector module 506, a module for interfacing with and controlling the image capture device 202, such as camera module 508, a module for storing image and measurement data for the captured images, such as camera data module 510, a module for managing machine learning models, such as machine learning model service module 512, a module for processing images using the machine learning models, such as machine learning processor 514, and/or a calculation engine 516.

In some examples, the measurement manager 502 may be responsible for controlling an overall wound measurement process. For example, the measurement manager 502 may control the wound scanning process by starting, stopping, and canceling measurements. In some examples, the measurement manager 502 may control the phase of the wound scanning process, for example, initializing the capture session, such as by initializing components of the image capture device 202. Illustrative embodiments of the measurement manager 502 may also selectively introducing delays into the wound scanning process, for example, to allow the user sufficient time to align the device with the wound. In some examples, the measurement manager 502 may hold the current state of the wound scanning process, for example, by storing states and measurements for processed images captured from the image capture device 202. In some embodiments, the measurement manager 502 may communicate with additional modules. For example, the measurement manager 502 may communicate with the wound detector module 506 in order to initialize an image capture session, start and stop a video preview from the image capture device 202, read captured images, depth maps, camera specific data, and wound masks and wound predictions.

According to illustrative embodiments, the audio and haptic feedback manager 504 may be responsible for providing audio and haptic feedback to the user during specific events in the scanning process. For example, the audio and haptic feedback manager 504 may contain instructions to cause the speaker assembly 322 to play a sequence of sounds, and/or cause the vibration motor 324, to play a sequence of vibrations. For example, at a beginning of a capture event, such as a capture session, the audio and haptic feedback manager 504 may cause the vibration motor 324 to play one quick vibration. In some examples, when a wound is correctly aligned with a camera, such as the image capture device 202, the audio and haptic feedback manager 504 may cause the speaker assembly 322 to play a sound and cause the vibration motor 324 to play two quick vibrations with ascending intensity. During a countdown event, such as while processing a captured image, evaluating wound alignment, and/or calculating wound dimensions, the audio and haptic feedback manager 504 may cause the speaker assembly 322 to play a sound. According to illustrative embodiments, when wound measurement is finished, the audio and haptic feedback manager 504 may cause the speaker assembly 322 to play a sound and the vibration motor 324 to play two quick vibrations with ascending intensity. In some examples, if wound measurement fails, the audio and haptic feedback manager 504 may cause the speaker assembly 322 to play a sound and the vibration motor 324 to play two quick vibrations with descending intensity.

In some embodiments, the wound detector module 506 may be responsible for detecting wounds on images capture by the image capture device 202. For example, the wound detector module 506 may initialize a capture session, start and stop video preview from the image capture device 202. The wound detector module 506 may also communicate with the machine learning processor 514 to request detection of a wound mask and/or predictions for images obtained from the image capture device 202. In some examples, the wound detector module 506 may communicate with the machine learning model service 512 to request the latest machine learning models from a server. For example, the wound detector module 506 and/or the machine learning model service 512 may communicate with the support center 114 by accessing the network 112 through the transceiver 310. Additionally or alternatively, the wound detector module 506 may create and return objects to the camera data module 510. For example, the wound detector module 506 may return data objects such as captured images, depth maps, camera intrinsic data, and calculated values to the camera data module 510.

According to illustrative embodiments, the camera data module 510 may initialize capture sessions, start and stop video previews displayed on the touchscreen 308, and return captured images and depth maps from the image capture device 202.

In some examples, the camera data module 510 may store captured images and measurement data for the images. For example, the camera data module 510 may store images captured from the image capture device 202, depth maps captured from the image capture device 202, intrinsic data such as image metadata from the image capture device 202, and wound masks and predictions from the machine learning processor 514. Additionally or alternatively, the camera data module 510 may convert depth maps from half-precision floating-point format (FP16 or float16) to single-precision floating-point format (FP32 or float32), and may call a calculation engine to calculate wound measurements.

In some examples, the machine learning model service 512 may be responsible for managing the machine learning models used by the machine learning processor 514. For example, the machine learning model service 512 may access the network 112 through the transceiver 310, and communicate with a server at the support center 114 or third party 122. The machine learning model service 512 may check the server for updated machine learning models, and update machine learning models stored locally on the mobile device 110 as necessary. If updates are necessary, the machine learning model service 512 may compile and validate the downloaded machine learning models. If no new models are available from the server or if the machine learning model service 512 cannot access the server, then the machine learning model service 512 may provide the machine learning processor 514 with locally stored machine learning models.

According to example embodiments, the machine learning processor 514 may be responsible for processing wound images captured by the image capture device 202. The machine learning processor 514 may detect wounds on the wound images, generate a wound mask corresponding with the detected wounds, and calculate predictions for the detected wounds. For example, the machine learning processor 514 may include a segmentation model for detecting a wound boundary and/or a wound mask from an input image, and an object detection model for detecting wound objects.

Figure 5B:
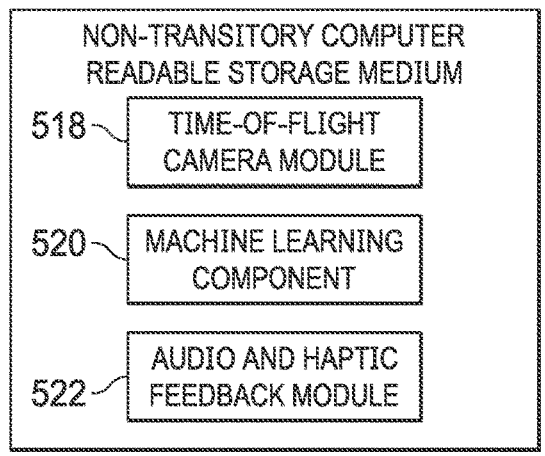
FIG. 5B is a schematic diagram illustrating examples of modules which may be stored on the non-transitory computer readable storage medium of FIG. 4 and which may be accessed by the processor and other components of the mobile device of FIGS. 1, 2, and 4.

FIG. 5B is a schematic diagram illustrating examples of modules which may be stored on the non-transitory computer readable storage medium 306 of FIG. 4 and which may be accessed by the processor 302 and other components of the mobile device 110 of FIGS. 1, 2, and 4. For example, the non-transitory computer readable storage medium 306 may contain a time-of-flight camera management module, such as time-of-flight camera module 518, a machine learning management and execution module, such as machine learning component 520, and a module managing audio and haptic feedback provided to the user, such as an audio and haptic feedback manager 522.

In some examples, the time-of-flight camera module 518 may be responsible for interfacing with and/or controlling the time-of-flight camera 402. For example, the time-of-flight camera 402 may utilize infrared light to measure the distance between it and objects within its field of view. The time-of-flight camera 402 may return data in Android dense depth image format (DEPTH16), with each pixel containing range or distance information and a confidence measure. Each pixel may be a 16-bit sample which represents a depth ranging measurement from a depth camera. The 16-bit sample may also include a confidence value representing a confidence of the sample.

According to some embodiments, the machine learning component 520 may include an object detection model for detecting wounds present in wound images, a post-processing model which takes object detection model outputs as an input and returns detected wound objects, and a segmentation model for detecting wound masks from an input image.

According to illustrative embodiments, the audio and haptic feedback manager 522 may cause the speaker assembly 322 to play a start sound at the beginning of a scanning process, such as a capture event, a countdown sound that plays every other second of the scanning process, an end sound that plays at the end of the scanning process, and an error sound that plays when an error occurs during the scanning process. Additionally or alternatively, the audio and haptic feedback manager module 522 may cause the vibration motor 324 to play two sequences of vibrations with increasing intensity at the beginning of the scanning process and/or at the end of the scanning process, and two sequences of vibrations with decreasing intensity at the end of the scanning process.

Figure 6:
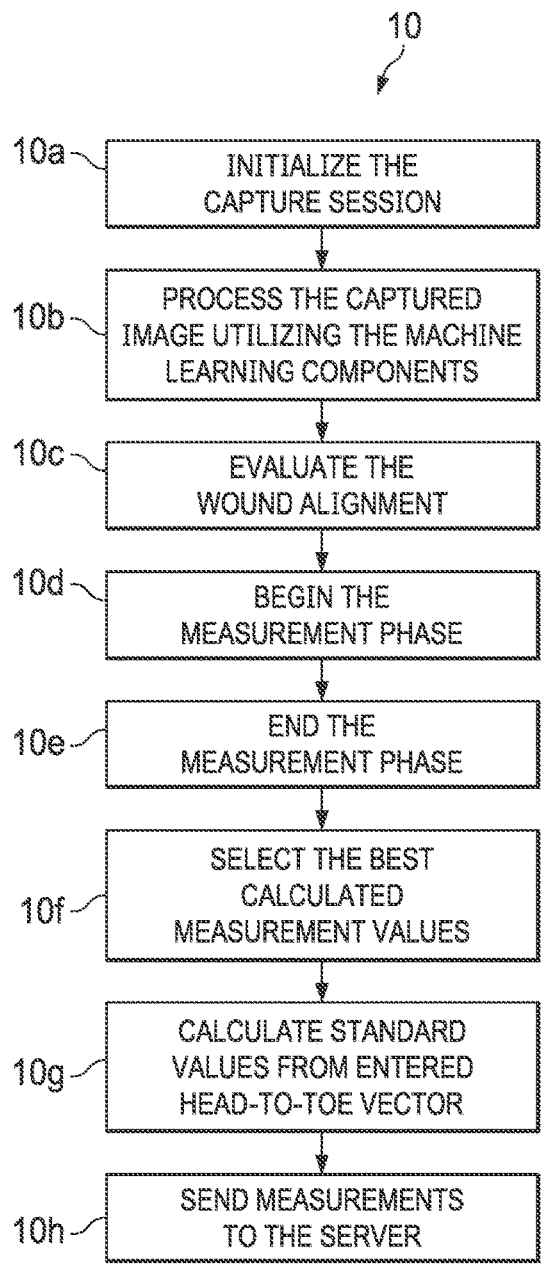
FIG. 6 is a flowchart of an exemplary process for capturing and processing a wound image from the image capture device of FIG. 2, FIG. 3, and FIG. 4.

FIG. 6 is a flowchart of an exemplary process 10 for capturing and processing a wound image from the image capture device 202 of FIG. 2, FIG. 3, and/or FIG. 4. At step 10a, a wound image capture session may be initialized. The wound detector module 506, camera module 508, and/or time-of-flight camera module 518 may obtain a continuous stream of wound images from the camera module 202 with associated depth maps or depth information. In some examples, the wound images may be individually captured still images. In some examples, the wound images may be still frame from a video stream. The captured wound images may be processed at step 10b with machine learning components, such as the machine learning processor 514 or machine learning component 520. The machine learning processor 514 or machine learning component 520 may detect wounds such as the tissue site 106 within the wound images, and calculate bounding boxes, wound masks, and wound boundaries for each wound of each wound image. In some examples, wounds may be detected and bounding boxes may be drawn utilizing an image or wound detection model. In some examples, the wound masks and wound boundaries may be generated using an image or wound segmentation model.

At step 10c, wound alignment may be calculated from the wound predictions, such as bounding boxes, wound masks, and/or wound boundaries. For example, the wound detector module 50, machine learning processor 514, and/or the machine learning component 520 may use the wound predictions to evaluate whether the wound is correctly aligned in the current wound images received from the image capture device 202. For example, if the wound is outside of the wound image, the touchscreen 308 may indicate that the wound is not correctly aligned. For example, an edge of a camera viewfinder reticle may be drawn as semi-transparent to indicate misalignment of a wound. In some examples, the audio and haptic feedback module 504 and/or 522 may alert the user of a misalignment. If all wounds are inside of the wound image, then a green checkmark may be displayed on the touchscreen 308, and/or the audio and haptic feedback module 504 and/or 522 may alert the user of correct alignment. After the wound is correctly aligned within the image capture device 202, the measurement phase may begin at step 10d.

At step 10d, wound images may be captured for a duration of time. For example, a single wound image may be captured and processed. In some embodiments, a plurality of wound images may be continuously captured and processed over the duration of time, for example, over an eight second interval. For each wound image, the associated wound mask, depth mask, camera specific data, and other wound predictions may be sent to the calculation engine 516. For each wound image, the calculation engine 516 may calculate measurement values, such as a mathematical length, mathematical width, depth, calculated area, geometric area, calculated volume, geometric volume, two normalized points for a length line, two normalized points for a width line, two normalized points for a depth line, and normalized points for a wound outline. In some examples, normalized points may be two-dimensional points with an x-component normalized to be in a range of 0 to 1, and a y-component normalized to be in a range of 0 to 1. For each wound image, the calculated measurement values may be stored in the memory 304 or on the non-transitory computer readable storage medium 306. After the period of time has elapsed, such as the eight second interval, the measurement phase may be ended at step 10e.

After the measurement phase is ended at step 10e, the best calculated measurement values may be selected at step 10f. If a single set of measurement values was captured for a single wound image at step 10d, the single set of measurement values may be selected by the calculation engine 516. If a plurality of measurement values is captured for a plurality of wound images, then the most accurate set of measurement values may be selected by the calculation engine 516. For example, median values and a standard deviation may be calculated for the entire set of the plurality of measurement values, such as length, width, and depth. For each measurement value of the set of the plurality of measurement values, an absolute difference may be calculated between that measurement value and the calculated median values. The measurement values with the lowest sum of absolute difference may be selected from the set of the plurality of measurement values, and the remaining measurement values may be discarded.

At step 10g, after the user enters a head-to-toe vector, standard wound dimensions may be calculated. For example, the head-to-toe vector may be a vector indicative of a direction from the head of the patient 104 to the toe of the patient 104. The wound standard length may be defined as the length of the wound at the longest point of the wound along the head-to-toe vector. The wound standard width may be defined as the widest point of the wound along a vector perpendicular to the head-to-toe vector. The wound standard depth may be defined as the deepest point of the wound. At step 10h, the wound measurements calculated at steps 10f and 10g may be sent via network 112 to a server.

Figure 7:
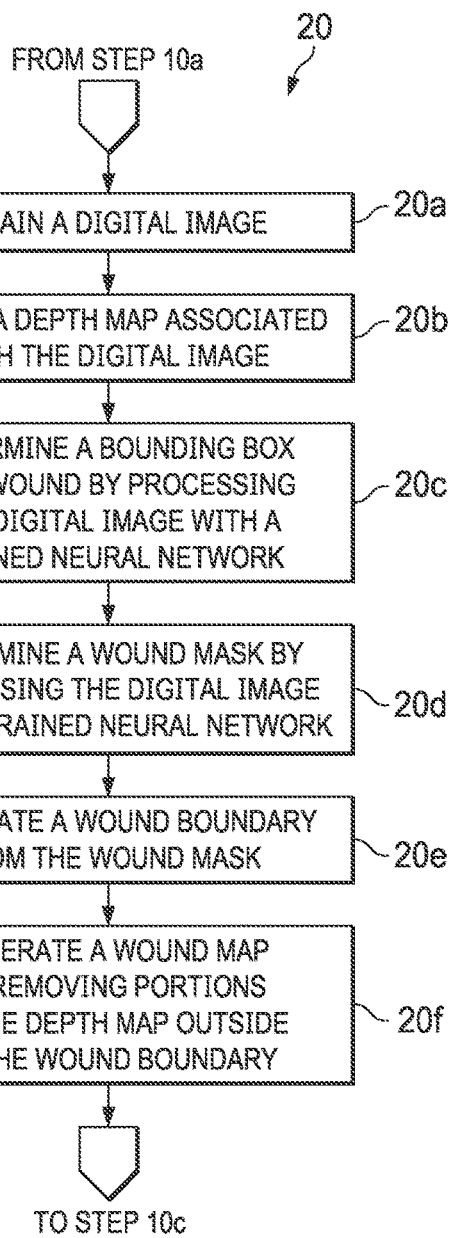
FIG. 7 is a flowchart of an exemplary process for processing a captured image utilizing machine learning components at step 10b of FIG. 6.

FIG. 7 is a flowchart of an exemplary process 20 for processing a captured image utilizing machine learning components at step 10b of FIG. 6. For example, after wound images and depth maps are captured at step 10a of process 10, the machine learning processor 514 and/or the machine learning component 520 may obtain a wound image, such as a digital image, from the image capture device 202 at step 20a. At step 20b, the machine learning processor 514 and/or the machine learning component 520 may obtain a depth map associated with the digital image. At step 20c, the machine learning processor 514 and/or the machine learning component 520 may apply a trained machine learning model, such as a wound detection model, in order to find all regions within the digital image where possible wounds are located. For example, the machine learning processor 514 and/or the machine learning component 520 may apply the trained wound detection model to provide a bounding box around each wound present on the digital image. At step 20d, the machine learning processor 514 and/or the machine learning component 520 may apply a trained machine learning model in order to determine a wound mask. For example, the wound mask may be a binary mask of the same size as the digital image. In some examples, if the value of a pixel of the binary mask is 1, the corresponding pixel in the digital image represents a wound. According to some embodiments, if the value of a pixel of the binary mask is 0, the corresponding pixel in the digital image does not represent a wound. At step 20e, after the wound mask has been generated, a wound boundary can be calculated based on the wound mask. For example, the wound boundary may be where the wound mask transitions from regions where the value of the pixels of the binary mask is 1 to regions where the value of the pixels is 0. At step 20f, a wound map may be generated by removing portions of the depth map outside of the wound boundary. In some examples, the wound map may be generated by removing portions of the depth map corresponding to regions of the wound mask where the value of the pixels is 0.

Figure 8:
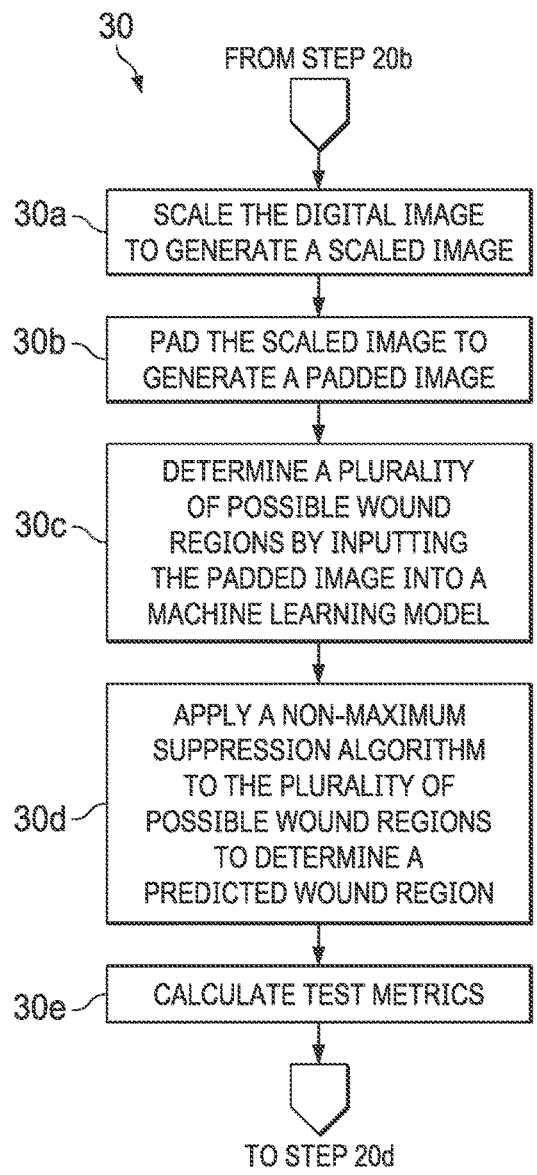
FIG. 8 is a flowchart of an exemplary process for determining a bounding box of a wound by processing a digital image with a trained neural network at step 20c of FIG. 7.

FIG. 8 is a flowchart of an exemplary process 30 for determining a bounding box of a wound by processing a digital image with a trained neural network at step 20c of FIG. 7. For example, after the machine learning processor 514 and/or the machine learning component 520 obtains the digital image from the image capture device 202 at step 20a and obtains the depth map associated with the digital image at step 20b, the digital image may be scaled to generate a scaled image at step 30a. For example, the scaled image may be a lower resolution version of the digital image. The scaled image should be of sufficient resolution for the trained machine learning model to distinguish between regions on the scaled image containing a wound and regions on the scaled image not containing a wound. At step 30b, the scaled image may be padded to generate a padded image. For example, if the width of the scaled image is not equal to the height of the scaled image, pixels may be added at the boundaries of the scaled image until the scaled image is a square. For example, after the digital image is scaled at step 30a and padded at step 30b, the size of the padded image may be a square having dimensions of 320 pixels by 320 pixels. In some examples, the width of the scaled image and the length of the scaled image should be in multiples of 32 pixels. For example, the size of the scaled image may be 256 pixels by 256 pixels, 320 pixels by 320 pixels, or 512 pixels by 512 pixels.

At step 30c, a trained machine learning model, such as a wound detection model, may be used to predict possible wound regions within the padded image. For example, a deep neural network, such as a convolutional neural network (CNN) may be used to analyze the padded image. In some examples, each possible wound region predicted by the trained machine learning model may be characterized by five values. For example, each possible wound region may include an $x_1$ value such as a relative X-coordinate of the upper-left corner of the predicted region, a $y_1$ value such as a relative Y-coordinate of the upper-left corner of the predicted region, an $x_2$ value such as a relative X-coordinate of the lower-right corner of the predicted region, a $y_2$ value such as a relative Y-coordinate of the lower-right corner of the predicted region, and a confidence score representing a confidence level of the model that a wound is actually present in the predicted region.

At step 30d, the predicted regions generated at step 30c may be filtered. For example, at step 30d, a non-maximum suppression algorithm may be applied to the plurality of possible wound regions to determine a single predicted wound region for each actual wound region. At step 30e, test metrics may be calculated. For example, test metrics may be used for measuring the performance of the trained machine learning model and informing users of the readiness of a machine learning model. In some embodiments, true positives (TP), false positives (FP), and false negatives (FN) can be calculated and summed for every image in a test dataset. For example, if the predicted region within an image in the test dataset has a Jaccard index or Intersection over Union (IoU) with a real region within the image in the test dataset higher than a threshold, then the predicted region and the real region should be paired, and the predicted region should be considered a true positive. This process may be repeated for all of the predicted regions. If the predicted region has an IoU with the real region lower than the threshold, then the predicted region should be considered a false positive. Real regions which are not detected may be considered false negatives. After the true positives, false positives, and false negatives have been calculated for every image, test metrics such as precision, recall, and the F-score ($F_1$) may be calculated according to equations 1-3 below:

$$\text{Precision} = \frac{TP}{TP + FP} \quad (1)$$

$$\text{Recall} = \frac{TP}{TP + FN} \quad (2)$$

$$F_1 = \frac{2 \cdot \text{Precision} \cdot \text{Recall}}{\text{Precision} + \text{Recall}} \quad (3)$$

Generally, the machine learning models with higher precision, recall, and $F_1$ values may be considered better trained and/or more ready.

Figure 9:
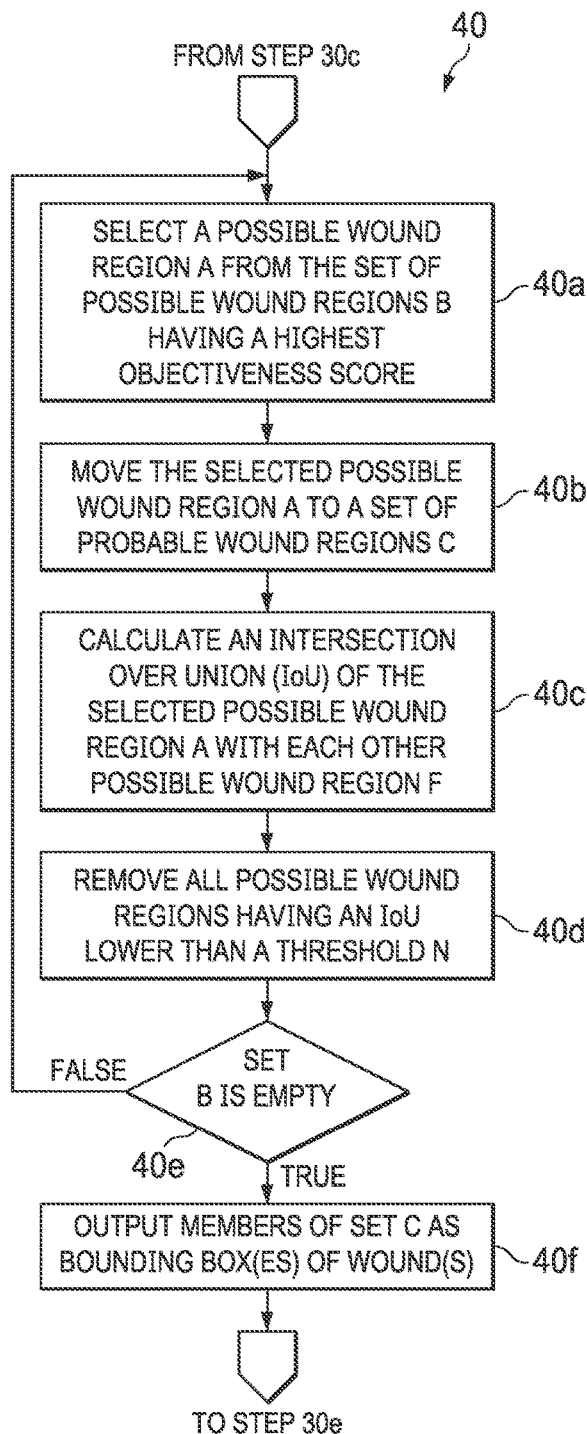
FIG. 9 is a flowchart of an exemplary process of a non-maximum suppression algorithm which may be applied at step 30d of FIG. 8.

FIG. 9 is a flowchart of an exemplary process 40 of a non-maximum suppression algorithm which may be applied at step 30d of FIG. 8. For example, after a plurality of possible wound regions have been determined by inputting the padded image into the trained machine learning model at step 30c, a possible wound region A may be selected form the set of possible wound regions B at step 40a. The selected possible wound region A should be the region within the set of possible wound regions B having the highest objectiveness score. For example, the selected possible wound region A may be the region within the set of possible wound regions B having the highest confidence score. At step 40b, the selected possible wound region A may be moved to a set of probable wound regions C. At step 40c, an IoU of the selected possible wound region A with each other possible wound region from the set of possible wound regions B may be calculated. At step 40d, all possible wound regions having an IoU lower than a threshold N may be removed from the set of possible wound regions B. At step 40e, if set B is not empty, then the steps of 40a through 40d may be repeated. If at step 40e, set B is empty, then the members of the set of probable wound regions C may be returned as the bounding boxes(s) of the wound(s).

Figure 10:
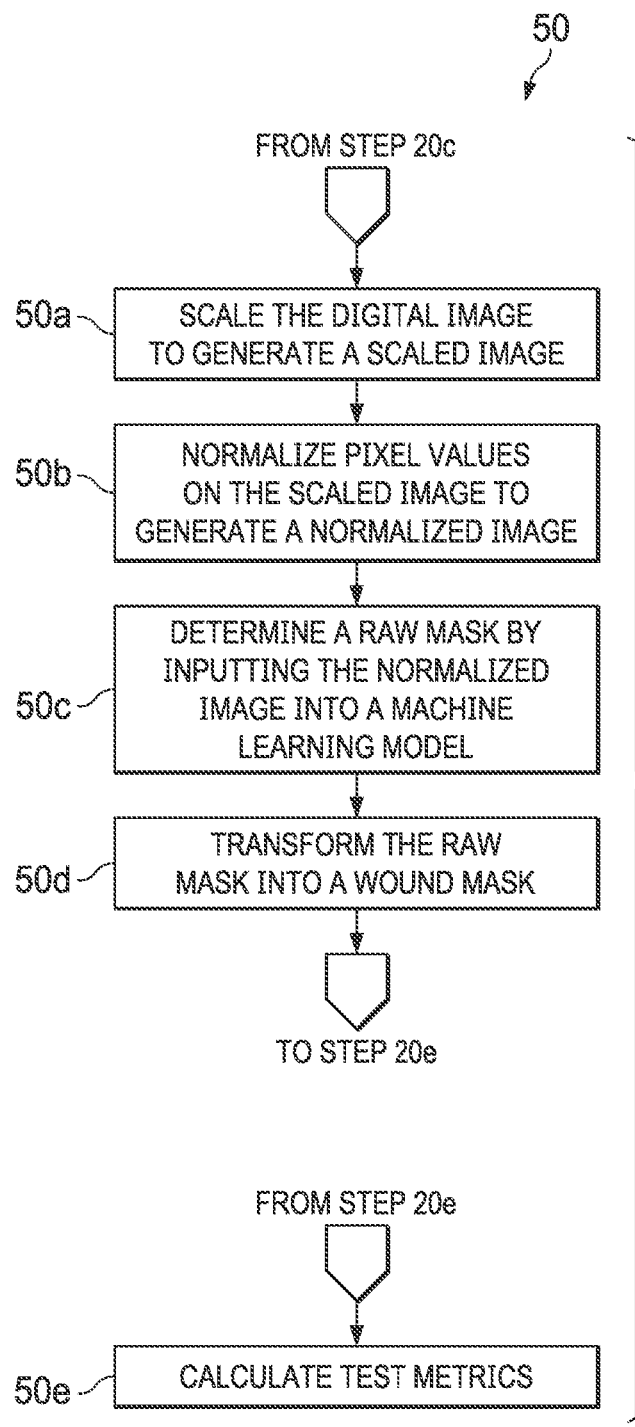
FIG. 10 is a flowchart of an exemplary process of determining a wound mask by processing a digital image with a trained neural network at step 20d of FIG. 7.

FIG. 10 is a flowchart of an exemplary process 50 of determining a wound mask by processing a digital image with a trained neural network at step 20d of FIG. 7. According to illustrative embodiments, after a bounding box has been determined at step 20c of FIG. 7, the digital image obtained at step 20a of FIG. 7 may be scaled to generate a scaled image at step 50a. For example, the digital image may be scaled down from its original size into a lower resolution. In some embodiments, the scaled image may have a size of 256 pixels by 256 pixels. In some examples, the width and the height of the scaled image should be in multiples of 32. For example, the scaled image may have a size of 320 pixels by 320 pixels, or 512 pixels by 512 pixels. At step 50b, the pixel values of the scaled image may be normalized to generate a normalized image. For example, the value of each pixel on the normalized image may be in a range of 0 to 1. In some examples, the value of each pixel on the normalized image may represent an intensity of the corresponding pixel on the scaled image. In some examples, the normalized image may represent a grayscale image of an RGB scaled image. At step 50c, the normalized image may be input into a trained machine learning model, such as a wound segmentation model, to determine a raw mask. For example, a CNN may be applied to analyze the normalized image. The trained machine learning model will generate a raw mask of the same size as the preprocessed image. In some examples, the value of each pixel of the raw mask may be a floating-point number in a range of 0 to 1. In some examples, the higher the value of a pixel of the raw mask is, the more likely it may be that the pixel is a part of a wound.

At step 50d, the raw mask may be transformed into a wound mask. For example, the wound mask may be a binary mask of the same size at the digital image obtained at step 20a of FIG. 7. If the value of a pixel of the binary mask is 1, the corresponding pixel of the digital image is likely a part of a wound. If the value of a pixel of the binary mask is 0, the corresponding pixel of the digital image is not likely to be part of a wound. After step 50d, a wound boundary may be calculated, for example, as previously described in step 20e of FIG. 7. After wound boundaries are calculated, test metrics may be calculated at step 50e. At step 50e, true positives, false positives, and false negatives may be calculated for each wound mask. For example, if a calculated wound boundary has an IoU with a real wound boundary higher than a threshold, then the calculated wound boundary and the real wound boundary may be paired, and the calculated wound boundary may be considered to be a true positive. If the calculated wound boundary has an IoU with a real wound boundary lower than the threshold, then the calculated wound boundary may be considered a false positive. If a real wound boundary does not intersect with a calculated wound boundary, than a false negative should be recorded. Precision, recall, and $F_1$ may be calculated according to previously described equations (1) through (3). As previously discussed, the machine learning models with higher precision, recall, and $F_1$ values may be considered better trained and/or more ready.

Figure 11:
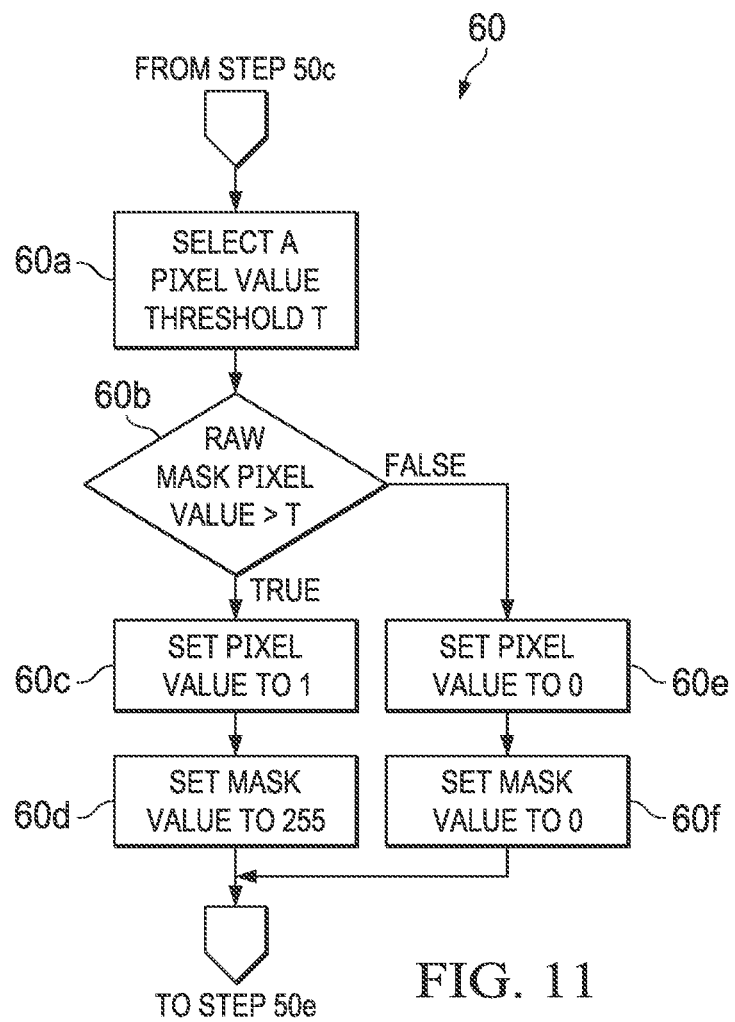
FIG. 11 is a flowchart of an exemplary process of transforming a raw mask into a wound mask at step 50d of FIG. 10.

FIG. 11 is a flowchart of an exemplary process 60 of transforming a raw mask into a wound mask at step 50d of FIG. 10. For example, after a raw mask has been determined by inputting the normalized image into the machine learning model at step 50c of FIG. 10, a pixel value T may be selected at step 60a. According to illustrative embodiments, a pixel value T of 0.5 may be selected. At step 60b, if the value of the pixel of the raw mask is greater than T, then the pixel value may be set to 1 at step 60c, and the mask value may be set to 255 at step 60d. At step 60b, if the value of the pixel of the raw mask is not greater than T, then the pixel value may be set to 0 at step 60e, and the mask value may be set to 0 at step 60f.

Figure 12:
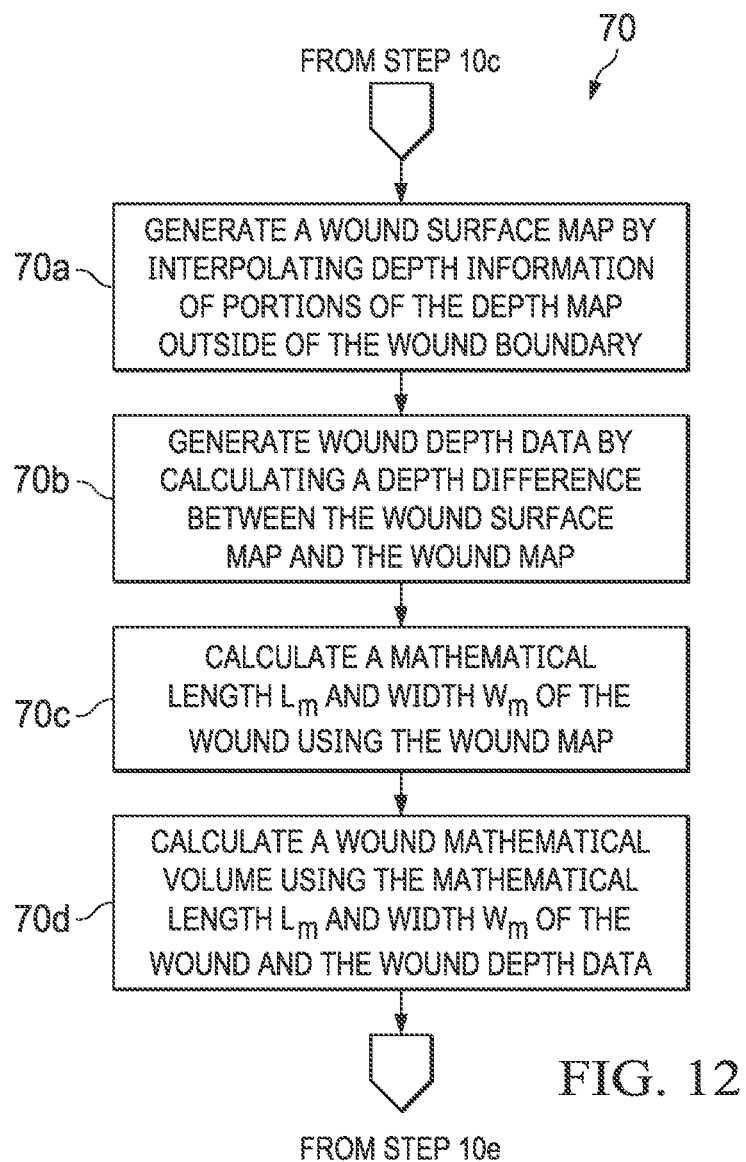
FIG. 12 is a flowchart of an exemplary process of calculating measurement values at step 10d of FIG. 6.

FIG. 12 is a flowchart of an exemplary process 70 of calculating measurement values at step 10d of FIG. 6. For example, at step 70a, a wound surface map may be generated by interpolating depth information of portion of the depth map outside of the wound boundary. The boundary of the wound surface map may be the wound boundary calculated form the wound mask at step 20e of FIG. 7. The depth of the wound surface map contained within the boundary of the wound surface map may be interpolated from the depth information of the depth map outside of the wound boundary. At step 70b, wound depth data may be generated by calculating a depth difference between the wound surface map and the wound map. At step 70c, the mathematical length L. and mathematical width Wm of the wound may be calculated using the wound map. At step 70d, a wound mathematical volume may be calculated using the mathematical length L. of the wound, mathematical width Wm of the wound, and the wound depth data.

Figure 13:
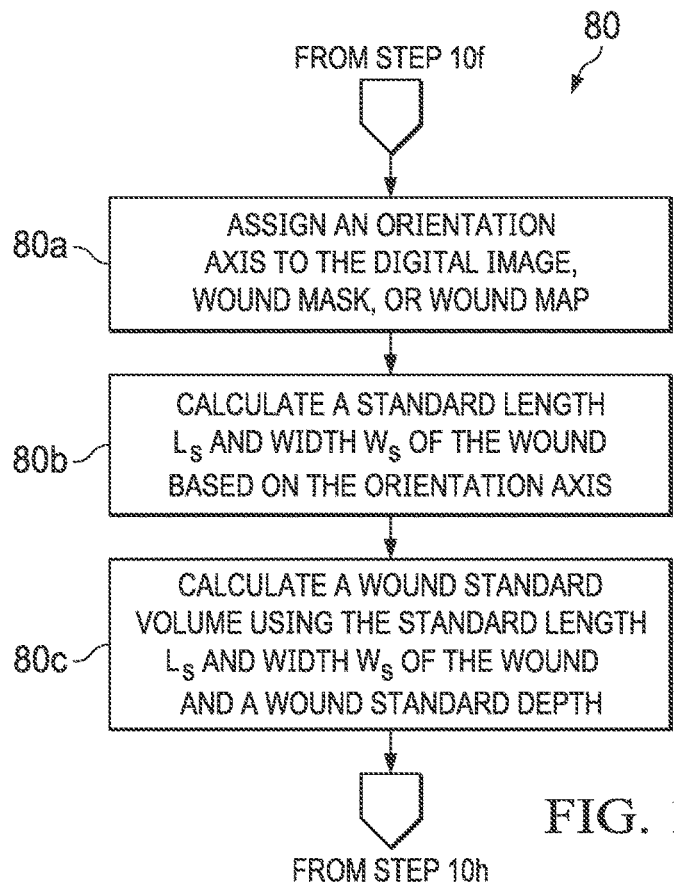
FIG. 13 is a flowchart of an exemplary process of calculating standard values at step 10g of FIG. 6.

FIG. 13 is a flowchart of an exemplary process 80 of calculating standard values at step 10g of FIG. 6. For example, at step 80a, an orientation axis may be assigned to the digital image, wound mask, and/or wound map. The orientation axis may be along the head-to-toe vector entered by the user. At step 80b, a standard length Ls and standard width $W_s$ may be calculated for the wound. As previously described, the wound standard length may be defined as the length of the wound at the longest point of the wound along the orientation axis, and the wound standard width may be defined as the widest point of the wound along a vector perpendicular to the orientation axis. At step 80c, the wound standard volume may be calculated using the wound standard depth, which may be defined as the deepest point of the wound.

Figure 14:
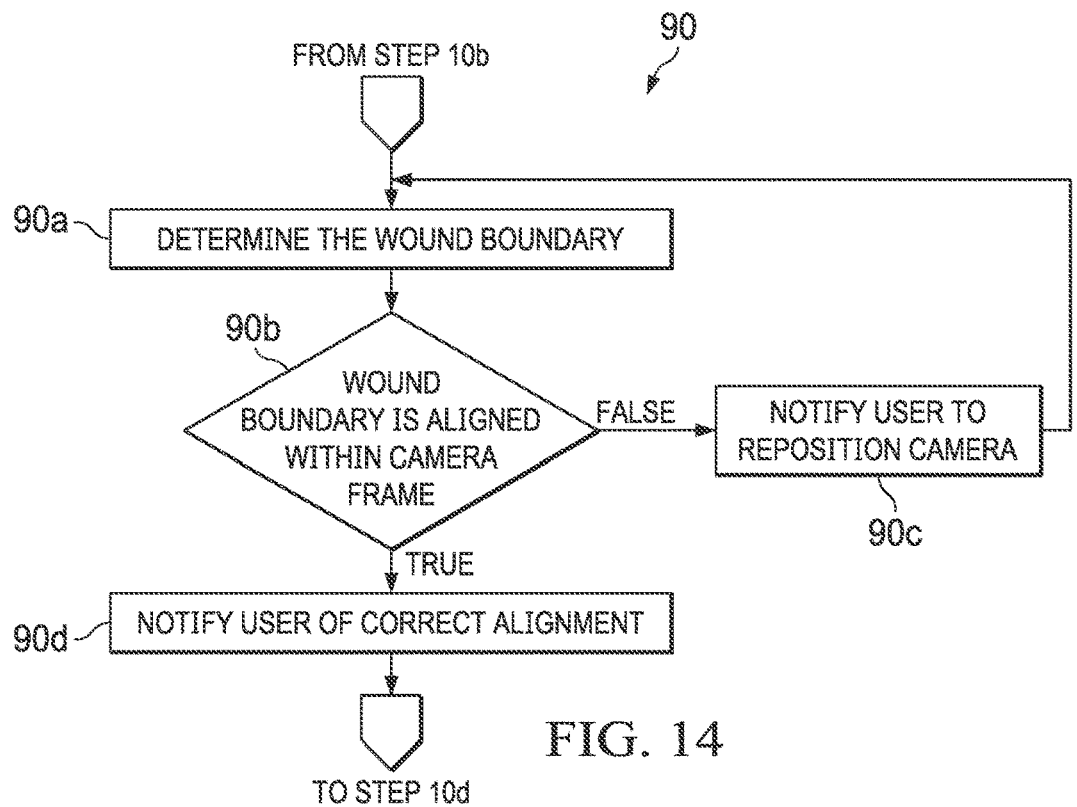
FIG. 14 is a flowchart of an exemplary process of notifying the user of correct image capture device alignment which may be performed at step 10c of FIG. 6.

FIG. 14 is a flowchart of an exemplary process 90 of notifying the user of correct image capture device 202 alignment which may be performed at step 10c of FIG. 6. In some examples, the image capture device 202 may be oriented in the same direction as the touchscreen 308. For example, the image capture device 202 may be the front-facing camera assembly of a smartphone. In use, the image capture device 202 may be pointed in the same direction as the touchscreen 308, for example, towards the wound. Process 90 provides a method for the user to align the image capture device 202 correctly with the wound without relying on a preview on the touchscreen 308. For example, at step 90a, the wound boundary may be determined. In some examples, the wound boundary calculated at step 20e of FIG. 7 may be used as the wound boundary at step 90a. At step 90b, the processor 302 determine whether the wound boundary is aligned with the camera frame of the image capture device 202. If at step 90b, the processor 302 determines that the wound boundary is not aligned within the camera frame, the mobile device 110 may notify the user to reposition the image capture device 202. For example, the processor 302 may send instructions to the speaker assembly 322 to audibly guide the user to reposition the mobile device 110, and/or the processor 302 may send instructions to the vibration motor 324 to vibrate when the wound is correctly aligned or when the wound is not correctly aligned. After step 90c, steps 90a and 90b are repeated until the processor 302 determines that the wound boundary is aligned with the camera frame at step 90b, upon which the mobile device 110 may notify the user that the image capture device 202 is correctly aligned, step 90d. For example, the processor 302 may send instructions to the speaker assembly 322 to play an audible sound indicating correct alignment, and/or the processor 302 may send instructions to the vibration motor 324 to notify the user of correct alignment through a series of vibrations.

Figure 15C:
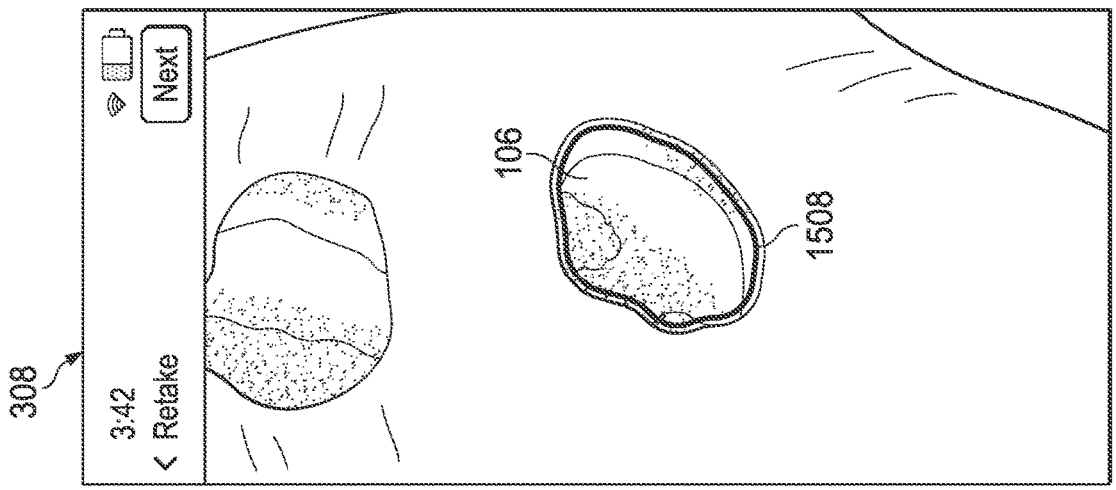
FIG. 15C shows an example of how the user interface may display the wound boundary calculated at step 20e of FIG. 7 to the user on the touchscreen.
Figure 15B:
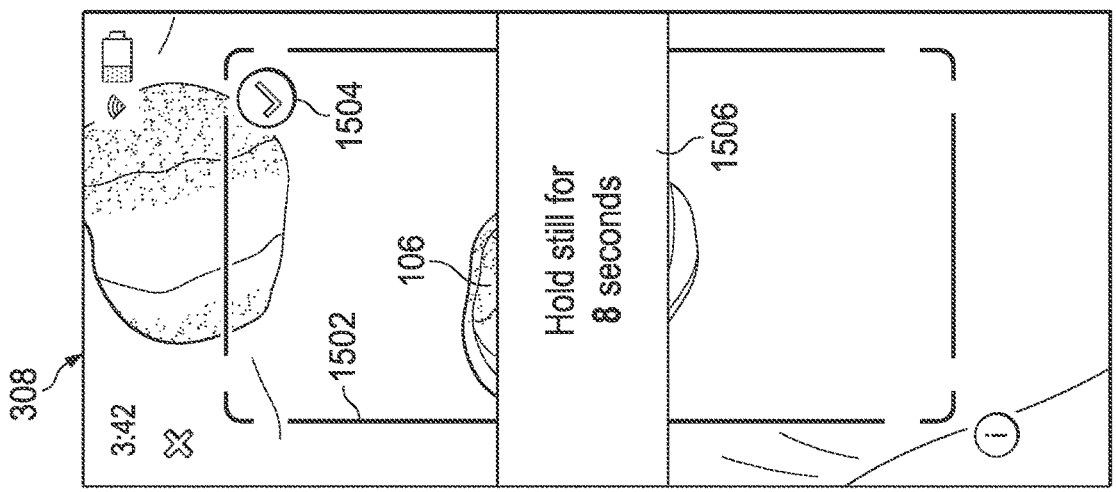
FIG. 15B shows an example of a message 1506 to the user to hold the image capture device still for the image capture interval.
Figure 15A:
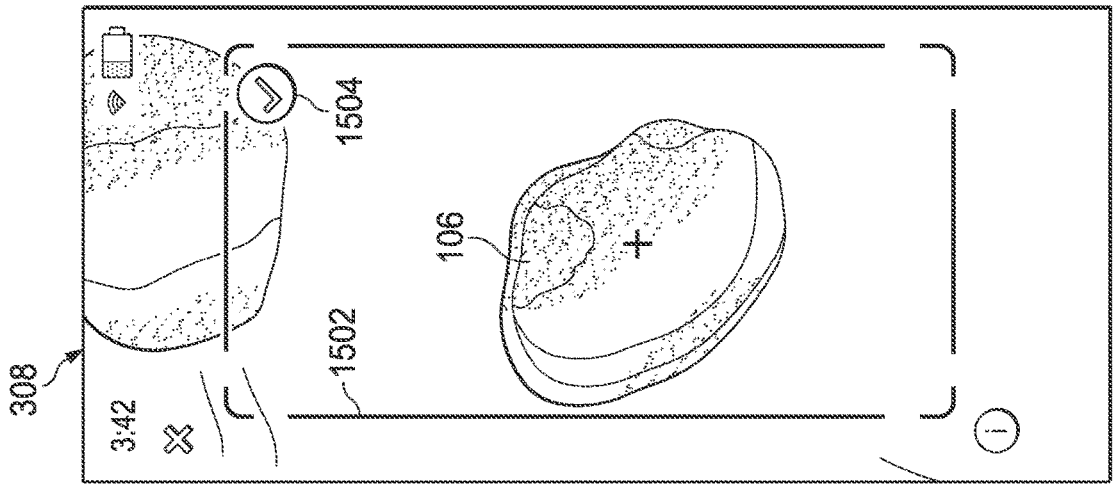
FIG. 15A illustrates examples of notifying the user of correct alignment at step 90d of FIG. 14 on the touchscreen 308.

Referring collectively to FIG. 15, example user interface adaptations displayed on examples of the touchscreen 308 the mobile device 110 of FIGS. 1-4 are shown. FIG. 15A illustrates examples of notifying the user of correct alignment at step 90d of FIG. 14 on the touchscreen 308. As shown in the upper right corner of the camera viewfinder frame 1502, a check mark 1504 may be shown when the image capture device 202 is correctly aligned with the wound, such as tissue site 106, at step 90d. FIG. 15B shows an example of a message 1506 to the user to hold the image capture device 202 still for the image capture interval. For example, if the measurement phase at step 10d of FIG. 6 includes continuously capturing wound images for an eight second interval, the user interface may display a message 1506 to "Hold still for 8 seconds" on the touchscreen 308, as shown in FIG. 15B. FIG. 15C shows an example of how the user interface may display the wound boundary calculated at step 20e of FIG. 7 to the user on the touchscreen 308.

As shown in FIG. 15C, the calculated wound boundary may be displayed as an outline 1508 overlaid on the wound.

Figure 16:
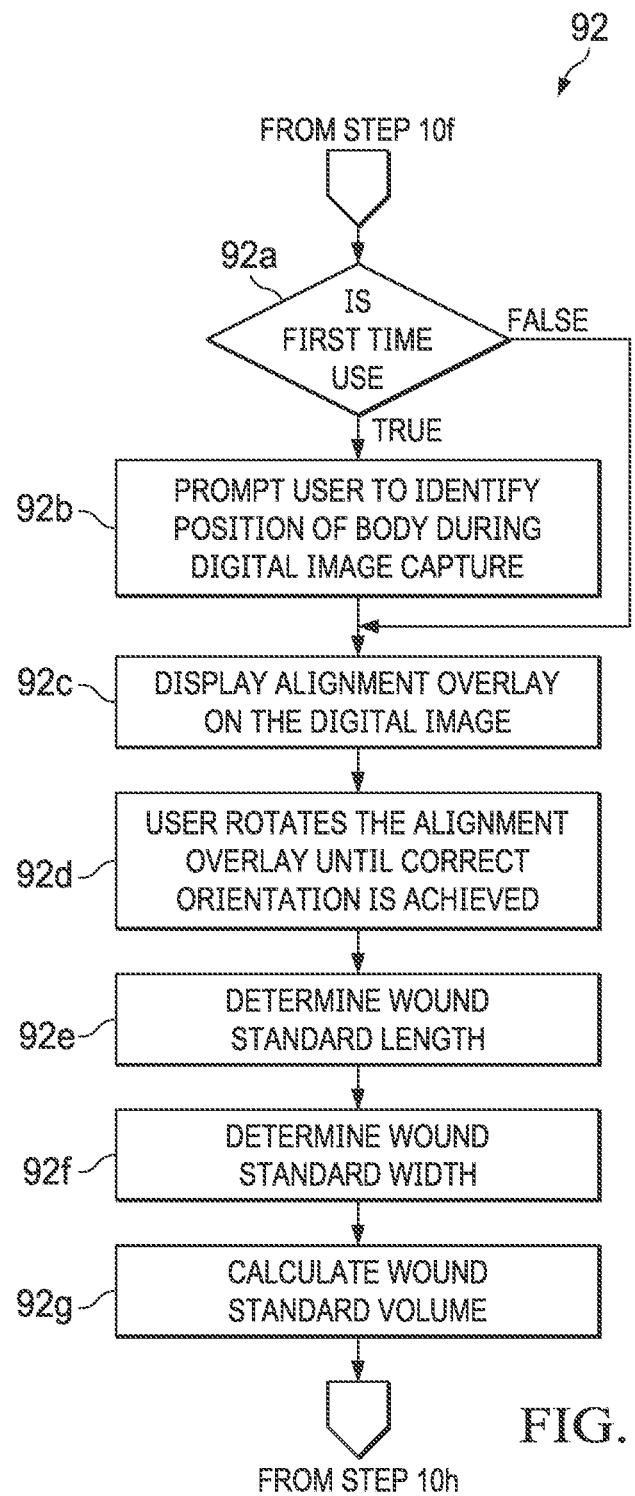
FIG. 16 is a flowchart of an exemplary process of the mobile device managing the process of the user inputting the head-to-toe vector and calculating standard values at step 10g of FIG. 6 and at FIG. 13.
Figure 17C:
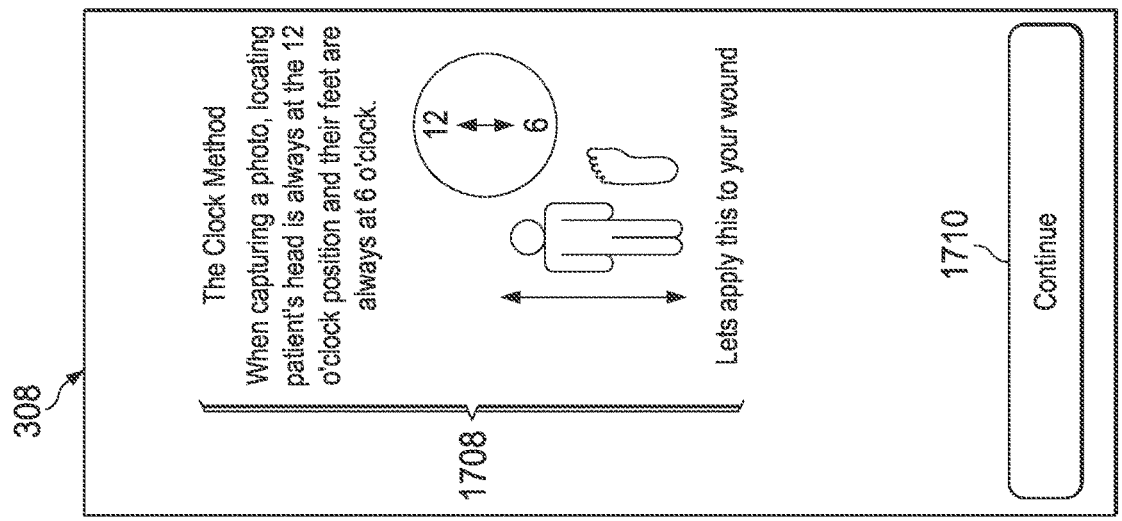
FIG. 17C shows an example of a user interface adaptation of the process of FIG. 16 displayed on examples of the touchscreen of the mobile device of FIGS. 1-4.
Figure 17B:
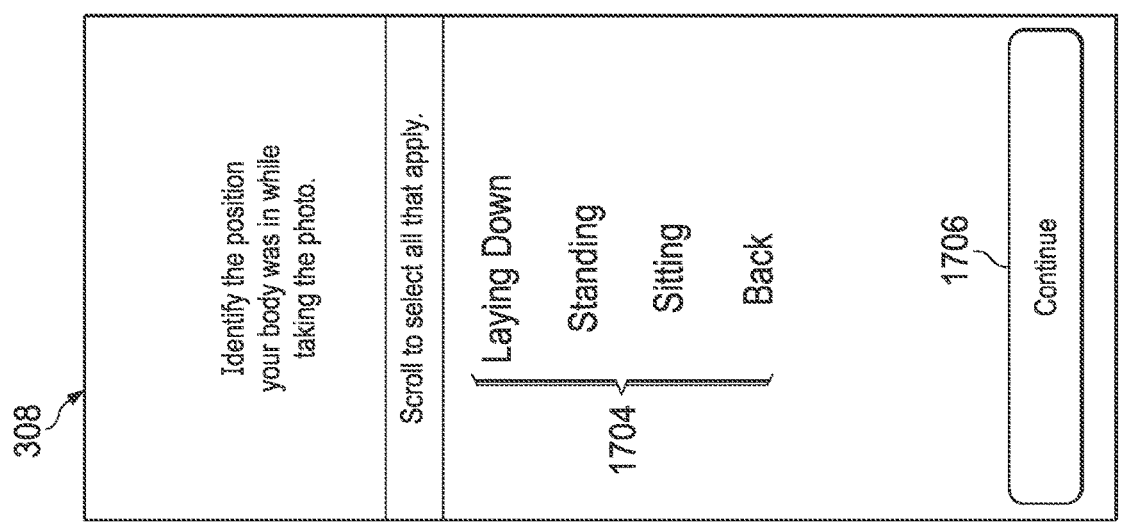
FIG. 17B shows an example of a user interface adaptation of the process of FIG. 16 displayed on examples of the touchscreen of the mobile device of FIGS. 1-4.
Figure 17A:
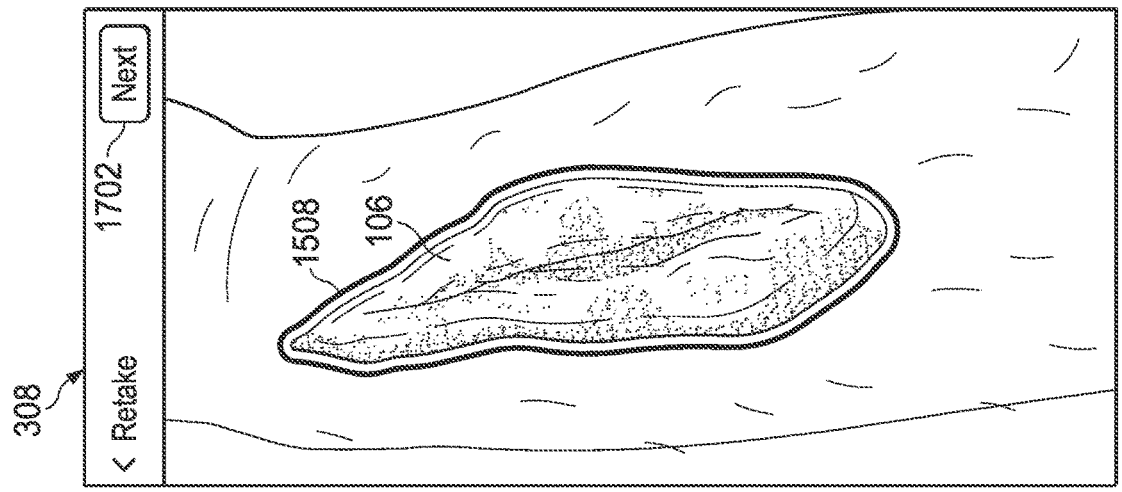
FIG. 17A shows an example of a user interface adaptation of the process of FIG. 16 displayed on examples of the touchscreen of the mobile device of FIGS. 1-4.

FIG. 16 is a flowchart of an exemplary process 92 of the mobile device 110 managing the process of the user inputting the head-to-toe vector and calculating standard values at step 10g of FIG. 6 and at FIG. 13. Referring collectively to FIG. 17, example user interface adaptations of the process 92 of FIG. 16 displayed on examples of the touchscreen 308 of the mobile device 110 of FIG. 1-4 are shown. For example, after step 10f of FIG. 6, an outline 1508 of the wound such as tissue site 106 may be shown on the touchscreen 308, along with a button 1702 for the user to continue. For example, as illustrated in FIG. 17A, a "Next" button 1702 may be shown in the upper right corner of the user interface. Upon the user selecting the "Next" button 1702, the processor 302 may determine whether it is a first time use scenario for the user at step 92a. If the processor 302 determines that it is a first time user scenario for the user at step 92a, the processor 302 may cause the touchscreen 308 to display a prompt 1704 to the user for the user to identify the position of the body during the wound image capture. For example, as illustrated in FIG. 17B, the touchscreen 308 may display a prompt 1704 asking the user to select whether the user's body was in a "Laying Down," "Standing," "Sitting" or on the "Back" position while the image capture device 302 was capturing the wound image. As shown in FIG. 17B, the user interface may include a button 1706 allowing the user to "Continue" after the user identifies the position of the body during the digital image capture at step 92b. After the user selects the "Continue" button 1706 in FIG. 17B, the process 92 may proceed to step 92c.

If at step 92b, the processor 302 determines that it is not a first time use case for the user, then the process 92 may proceed to step 92c. At step 92c, the processor 302 may cause the touchscreen 308 to display an alignment overlay. As shown in FIG. 17C, the user interface may display a screen explaining the "Clock Method" to the user. For example, as shown in FIG. 17C, the user interface may display text and graphics 1708 to explain to the user that according to the "Clock Method," the patient's head is located at the 12 o'clock position while the patient's feet are located at the 6 o'clock position. After the user selects the "Continue" button 1710 shown at the bottom of FIG. 17C, the processor 302 may display additional instructions 1712 on the touchscreen 308. For example, as shown in FIG. 17D, the processor 302 may cause the touchscreen 308 to display additional instructions prompting the user to "Rotate the hands of the clock to the position of your head '12 o'clock' and feet '6 o'clock.'" FIG. 17E shows an example of the alignment overlay 1704 displayed on the digital wound image received from the image capture device 202. At step 92d, the process 92, the user may rotate the alignment overlay 1714 shown in FIG. 17E until the correct orientation is achieved. The head-to-toe vector used by the process 10 at step 10g may be indicated by the line 1716 pointing to the 12 and 6 on the alignment overlay shown in FIG. 17E. At step 92e, the wound standard length may be determined as previously described with respect to step 10g of FIG. 6 and step 80b of FIG. 13. At step 92f, the wound standard width may be determined as previously described with respect to step 10g of FIG. 6 and step 80b of FIG. 13. At step 92g, the wound standard volume 92g may be determined as previously described with respect to step 10g of FIG. 6 and step 80c of FIG. 13.

Figure 17F:
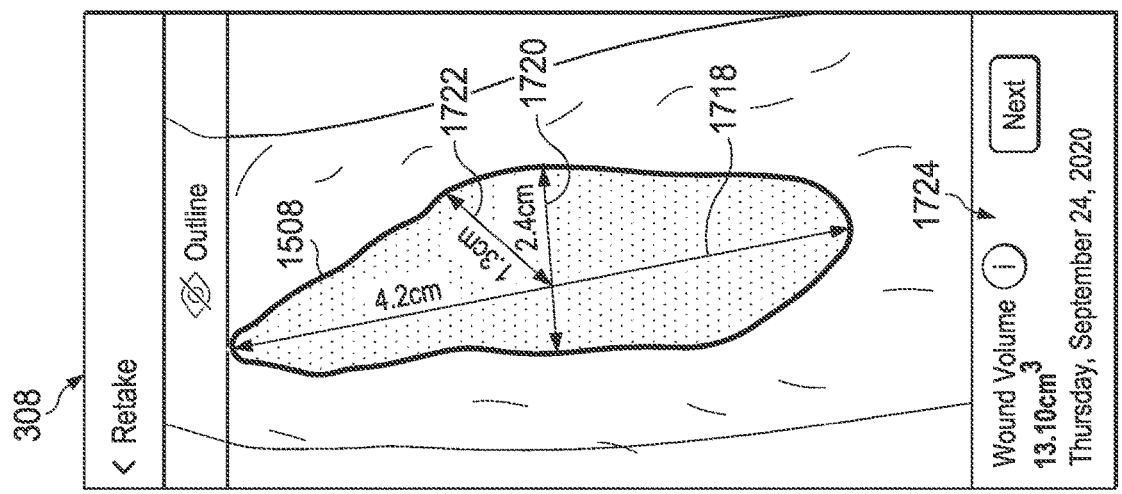
FIG. 17F shows an example of a user interface adaptation of the process of FIG. 16 displayed on examples of the touchscreen of the mobile device of FIGS. 1-4.
Figure 17E:
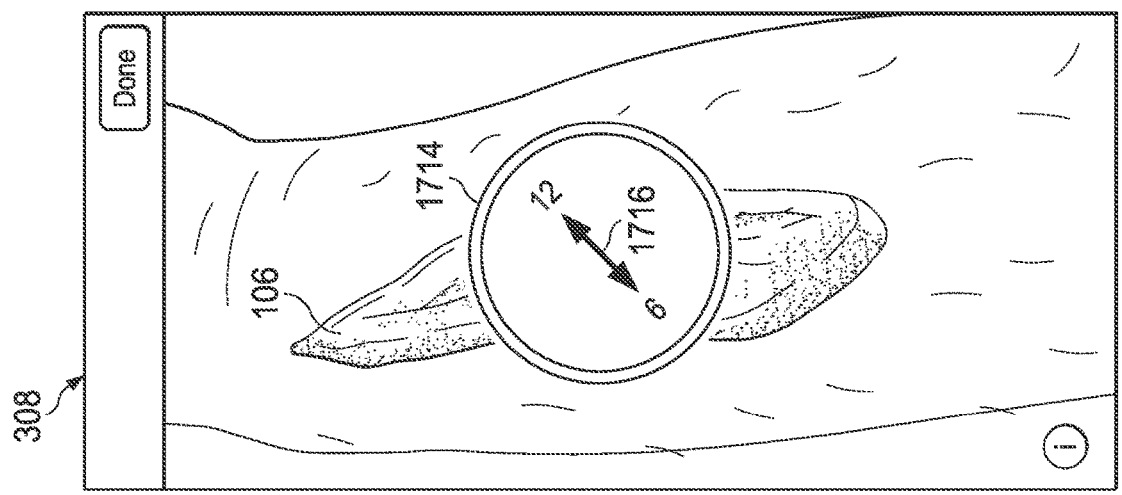
FIG. 17E shows an example of a user interface adaptation of the process of FIG. 16 displayed on examples of the touchscreen of the mobile device of FIGS. 1-4.
Figure 17D:
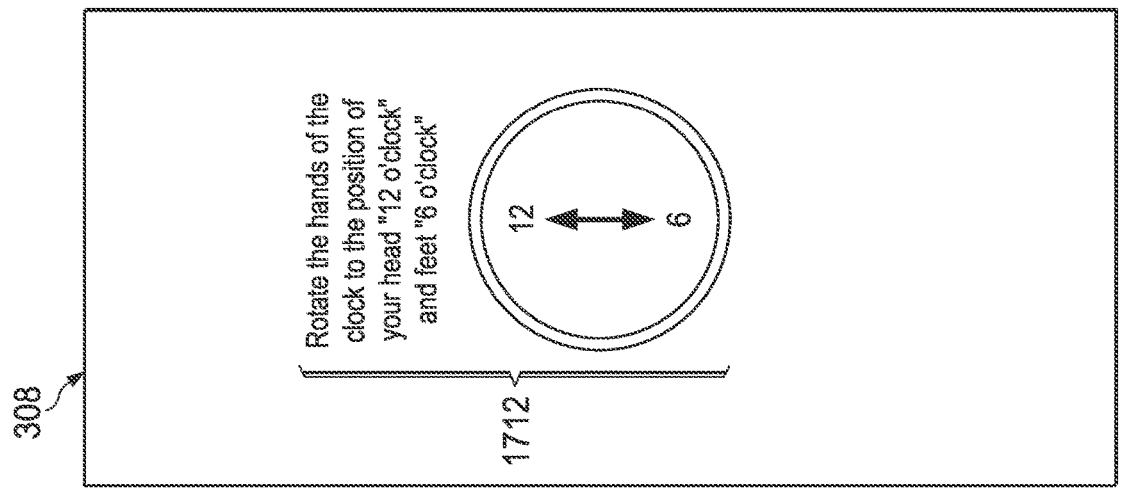
FIG. 17D shows an example of a user interface adaptation of the process of FIG. 16 displayed on examples of the touchscreen of the mobile device of FIGS. 1-4.
Figure 17G:
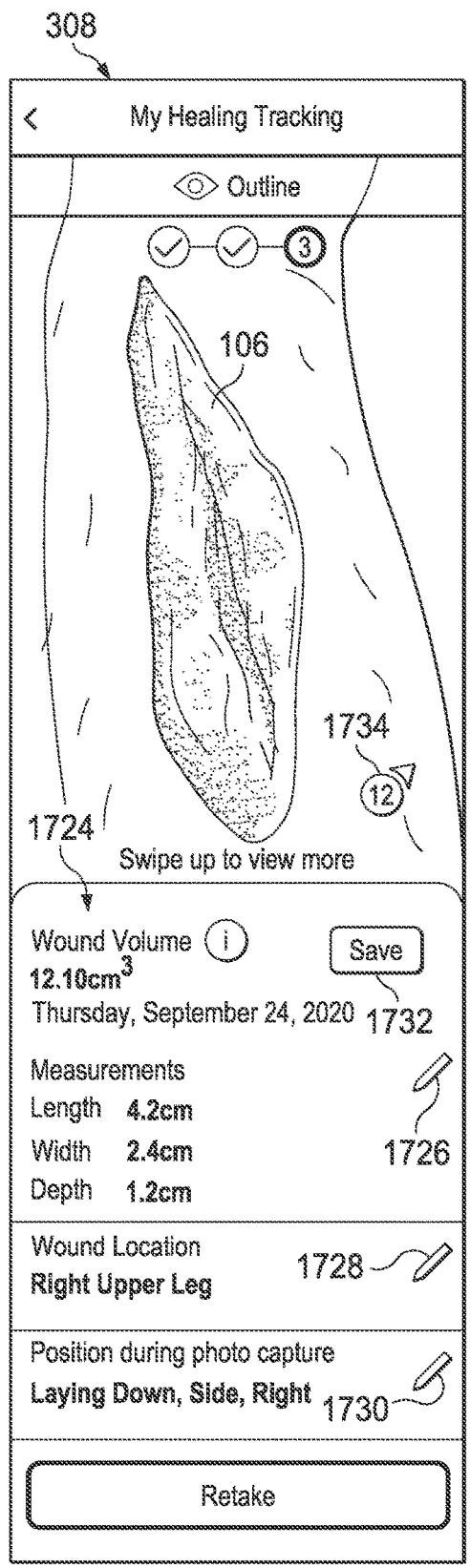
FIG. 17G shows an example of a user interface adaptation of the process of FIG. 16 displayed on examples of the touchscreen of the mobile device of FIGS. 1-4.
Figure 17H:
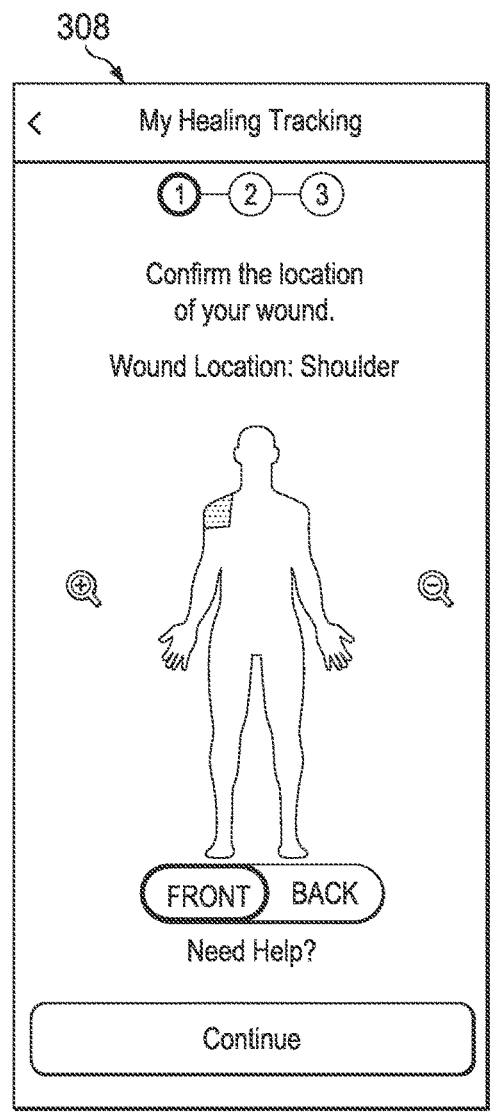
FIG. 17H shows an example of a user interface adaptation of the process of FIG. 16 displayed on examples of the touchscreen of the mobile device of FIGS. 1-4.
Figure 17I:
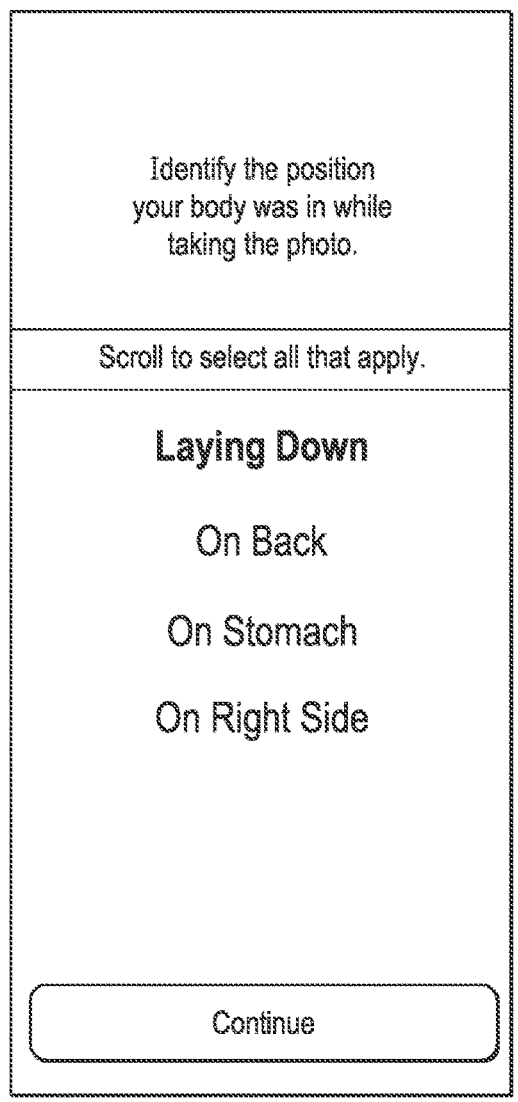
FIG. 17I shows an example of a user interface adaptation of the process of FIG. 16 displayed on examples of the touchscreen of the mobile device of FIGS. 1-4.

FIG. 17F shows an example user interface adaptation displaying the best calculated measurement values selected at step 10f of FIG. 6, such as the mathematical length, width, and volume calculated at steps 70c and 70d of FIG. 12. FIG. 17F also shows and the calculated standard values of step 10g of FIG. 6, such as the wound standard length, width, and volume calculated at steps 80b and 80c of FIG. 13 and steps 92e, 92f, and 92g of FIG. 16. As illustrated in FIG. 17F, the wound mathematical length may be overlaid on the wound image, for example, by the line 1718 labeled "4.2 cm." The wound mathematical width may be overlaid on the wound image, for example, by the line 1720 labeled "2.4 cm." The wound standard length may be overlaid on the wound image, for example, indicated by the line 1722 labeled "1.3 cm." In some examples, the wound mathematical volume may be shown, for example, in an expandable box 1724 at the bottom of the user interface shown in FIG. 17F. For example, the wound mathematical volume may be indicated below the text "Wound Volume" by "12.10 $cm^3$" along with the date the measurement was taken, indicated by "Thursday, Sep. 24, 2020." In some examples, the expandable box 1724 at the bottom of the user interface in FIG. 17F may be expanded to display more information. For example, as shown in FIG. 17G, the user may use the touchscreen 308 in order to drag or swipe the expandable box 1724 up to additionally display "Measurements," which may include the mathematical length "Length 4.2 cm," mathematical width "Width 2.4 cm," and depth "Depth 1.2 cm." Additionally, a "Wound Location," such as the "Right Upper Leg" may be displayed, as well as the "Position during photo capture," such as "Laying Down, Side, Right." If the user selects the stylus 1726 in the "Measurements" field, the wound measurements may be manually edited. If the user selects the stylus 1728 in the "Wound Location" field, the user may confirm or edit the location of the wound, FIG. 17H. If the user selects the stylus 1730 in the "Position during photo capture" field, the user may confirm or edit the position the patient's body was in while the wound image was captured, FIG. 17I. After the user has confirmed or edited the fields shown in FIG. 17G, the user may select the "Save" button 1732 to save the measurements and data. In some examples, a miniaturized indicator 1734 may show the head-to-toe vector at any screen of the user interface.

Figure 18:
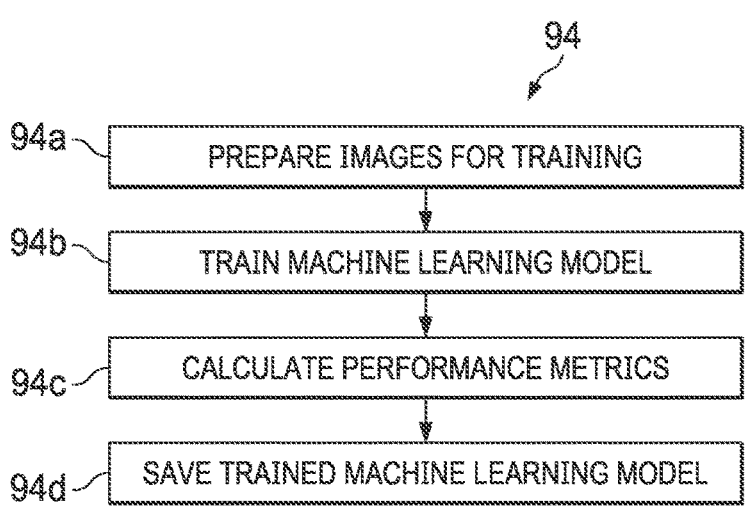
FIG. 18 is a flowchart of an exemplary process for training a machine learning model for use in the processes of FIGS. 6, 7, 8, and 10.

FIG. 18 is a flowchart of an exemplary process 94 for training a machine learning model for use in the processes of FIGS. 6, 7, 8, and 10. For example, process 94 may be used to train the wound detection model described with respect to FIGS. 6, 7, and 8, and/or the wound segmentation model described with respect to FIGS. 6, 7, and 10. At step 94a, the data, such as wound images, may be prepared for training. In some examples, the data may be prepared for training at a server, such as the server of the at the support center 114. The wound images should be annotated. For example, the wound images may be annotated with fields such as a presence of wounds and a number of wounds present. At step 94b, the machine learning model may be trained. For example, the machine learning model may be trained at the server. The annotated wound images may be loaded and used for training. After each training interval, the intermediate results of the training such as values of metrics and loss functions may be saved to a database. The learning curves of models during training may be used to diagnose problems with learning, such as an underfit model or an overfit model, as well as whether the training and validation datasets are suitably representative. In some examples, users may manually review images containing wound masks for training. According to illustrative embodiments, images with low confidence scores may be flagged for manual review. In some examples, wound masks may be manually adjusted during step 94b. Wound masks that have been manually adjusted may be sent back to mobile devices 110, and users may be notified that the wound mask has been manually adjusted. At step 94c, performance metrics can be calculated. For example, performance metrics may be calculated at the server. When the machine learning model has been trained, metrics may be calculated to compare the performance of the trained model against existing ones. For example, metrics similar to the test metrics described with respect to step 30e of FIG. 8 and/or step 50e of FIG. 10 may be used. At step 94d, the trained machine model may be saved onto the server at the support center 114 for retrieval by the mobile device 110.

The systems, apparatuses, and methods described herein may provide significant advantages. For example, conventional methods of wound measurement, such as using rulers and cotton swabs, may be inaccurate. Similarly, existing methods of wound measurement using conventional two-dimensional cameras may require positioning an object of known dimensions within the frame for calibration. By utilizing an image capture device 202 capable of generating a depth map in addition to a digital image, the mobile device 110 may eliminate or substantially reduce human error associated with using rulers and cotton swabs or conventional two-dimensional cameras. Additionally, conventional two-dimensional cameras do not have the ability to determine depth. Thus, additional depth measurements or estimations may be required to estimate wound volume given a two-dimensional image. Furthermore, by utilizing a trained machine learning model, the process of imaging and measuring wounds with the mobile device 110 may be highly automated, reducing workload for clinicians and patients and increasing precision and accuracy. Additionally, in examples where the image capture device 202 includes specialized camera attachments, oxygenation of the wound may be detected. By using the image capture device 202 in conjunction with colorimetric, infrared, and/or fluorescent imaging, the presence of specific gram negative or gram negative bacteria may be detected in the wound site. Furthermore, the mobile device 110 may provide the user with a report of wound healing progress, and offer wound dressing recommendations to the user based on collected data. In some examples, the machine learning models may also be trained to classify the recognized wounds into the Red-Yellow-Black classification system based on appearance of the wound bed. Furthermore, the mobile device 110 may automatically provide wound volume data to a fluid instillation system in order to automatically calculate instillation fluid volume.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may also be combined or eliminated in various configurations for purposes of sale, manufacture, assembly, or use.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A system for measuring a wound site, comprising:
an image capture device;
a touchscreen;
a vibration motor; and
a processor;
wherein the image capture device is configured to:
   capture a digital image, and
   capture a depth map associated with the digital image;
wherein the processor is configured to:
   determine a bounding box of the wound site by processing the digital image with a first trained neural network,
   determine a wound mask by processing the digital image with a second trained neural network,
   determine a wound boundary from the wound mask,
   determine whether the wound boundary is aligned within a camera frame, and
   generate a wound map from the depth map, wound mask, and wound boundary;
wherein the processor and vibration motor are configured to:
   provide a series of vibrations at the vibration motor in response to the processor determining that the wound is aligned within the camera frame.

2. The system of claim 1, wherein the processor is further configured to:
scale the digital image to generate a scaled image;
pad the scaled image to generate a padded image;
determine a plurality of possible wound regions by inputting the padded image into the first trained neural network; and
determine the bounding box by applying a non-maximum suppression algorithm to the plurality of possible wound regions.

3. The system of claim 2, wherein the processor is further configured to:
select a selected possible wound region from the plurality of possible wound regions,
   wherein the selected possible wound region has a highest objectiveness score within the plurality of possible wound regions;
move the selected possible wound region to a set of probable wound regions;
calculate an Intersection over Union of the selected possible wound region with each possible wound region in the plurality of possible wound regions; and
remove each possible wound region in the plurality of possible wound regions having an Intersection over Union with the selected possible wound region lower than a threshold.

4. The system of claim 1, wherein the processor is further configured to:
scale the digital image to generate a scaled image;
normalize pixel values of the scaled image to generate a normalized image;
determine a raw mask by inputting the normalized image into the second trained neural network; and
transform the raw mask into a wound mask.

5. The system of claim 4, wherein the processor is further configured to:
select a pixel value threshold;
set values of raw mask pixels greater than the pixel value threshold to 1; and
set values of raw mask pixels not greater than the pixel value threshold to 0.

6. The system of claim 5, wherein the processor is further configured to:
set values of raw mask pixels having a value of 1 to 255; and
output the raw mask as the wound mask.

7. The system of claim 1, wherein the processor is further configured to:
generate a wound surface mask by interpolating depth information of portions of the depth map outside of the wound boundary;
generate wound depth data by calculating a depth difference between the wound surface map and the wound map;
calculate a mathematical length of the wound and a mathematical width of the wound from the wound map; and
calculate a wound mathematical volume from the mathematical length of the wound, the mathematical width of the wound, and depth data of the wound map.

8. The system of claim 7, wherein the processor is further configured to:
assign an orientation axis to the wound map;
calculate a standard length of the wound and a standard width of the wound from the wound map and the orientation axis;
determine a standard depth of the wound from the wound map; and
calculate a standard wound volume from the standard length of the wound, the standard width of the wound, and the standard depth of the wound.

9. The system of claim 1, wherein the series of vibrations comprises two quick vibrations with ascending intensity.

10. The system of claim 1, wherein the processor and touchscreen are configured to:
display a visual indicator on the touchscreen in response to the processor determining that the wound is aligned within the camera frame.

11. The system of claim 1, further comprising:
a speaker assembly;
wherein the processor and speaker assembly are configured to:
   output an audible alert from the speaker assembly in response to the processor determining that the wound is aligned within the camera frame.

12. The system of claim 1, further comprising:
a speaker assembly;
wherein the processor and speaker assembly are configured to:
   output an audible alert from the speaker assembly in response to the processor determining that the wound is not aligned within the camera frame.

13. The system of claim 1, wherein the image capture device comprises:
an electro-optical camera;
an infrared camera; and
a light emitting module.

14. The system of claim 13, wherein the light emitting module is configured to emit multiple light rays according to a pattern.

15. The system of claim 1, wherein the image capture device comprises:
an electro-optical camera; and
a time-of-flight camera.

16. A non-transitory computer-readable medium comprising executable instructions for performing steps in a method for measuring a wound site, wherein the executable instructions configure a processor:
receive a digital image;
receive a depth map associated with the digital image;
determine a bounding box of the wound site by processing the digital image with a first trained neural network;
determine a wound mask by processing the digital image with a second trained neural network;
determine a wound boundary from the wound mask;
determine whether the wound boundary is aligned within a camera frame; and
generate a wound map from the depth map, wound mask, and wound boundary.

17. The non-transitory computer-readable medium of claim 16, wherein the executable instructions further configure the controller to:
output a signal to generate a first series of vibrations at a vibration motor in response to the processor determining that the wound is aligned within the camera frame.

18. A method for measuring a wound site, comprising:
capturing a digital image of the wound site with an image capture device;
capturing a depth map associated with the digital image with the image capture device;
determining a bounding box of the wound site by processing the digital image with a first trained neural network;
determining a wound mask of the wound site by processing the digital image with a second trained neural network;
determining a wound boundary from the wound mask;
generating a wound map from the depth map, wound mask, and wound boundary;
determining whether the wound boundary is aligned within a camera frame; and
providing a series of vibrations at a vibration motor if the wound is aligned within the camera frame.

19. The method of claim 18, wherein the series of vibrations comprises two quick vibrations with ascending intensity.

20. The method of claim 18, further comprising outputting an audible alert from a speaker assembly if the wound boundary is aligned within the camera frame.

* * * * *